United States Patent [19]
Lubisch et al.

[11] Patent Number: 6,103,720
[45] Date of Patent: Aug. 15, 2000

[54] KETOBENZAMIDES AS CALPAIN INHIBITORS

[75] Inventors: Wilfried Lubisch, Mannheim; Achim Möller, Grünstadt; Hans-Jörg Treiber, Brühl, all of Germany

[73] Assignee: BASF Aktiengesellschaft, Ludwigshafen, Germany

[21] Appl. No.: 09/319,511

[22] PCT Filed: Nov. 28, 1997

[86] PCT No.: PCT/EP97/06655

§ 371 Date: Jun. 8, 1999

§ 102(e) Date: Jun. 8, 1999

[87] PCT Pub. No.: WO98/25883

PCT Pub. Date: Jun. 18, 1998

[30] Foreign Application Priority Data

Dec. 11, 1996 [DE] Germany ............... 196 51 316

[51] Int. Cl.[7] ............... A61K 31/535; A61K 31/495; A61K 31/21; C07D 241/36; C07D 233/54
[52] U.S. Cl. ............... 514/237.8; 514/249; 514/311; 514/319; 514/399; 514/506; 546/162; 546/169; 546/195; 544/355; 548/338.1; 560/24; 560/33
[58] Field of Search ............... 560/24, 33; 548/338.1; 546/162, 195, 169; 544/355; 514/506, 399, 237.8, 319, 249, 361

[56] References Cited

U.S. PATENT DOCUMENTS 5,162,500 11/1992 Takeuchi et al. ............... 530/330
5,496,927 3/1996 Kolb et al. ............... 530/328

FOREIGN PATENT DOCUMENTS

| 520 336 | 12/1992 | European Pat. Off. . |
| 91/09801 | 7/1991 | WIPO . |
| 92/11850 | 7/1992 | WIPO . |
| 92/12150 | 7/1992 | WIPO . |
| 94/00095 | 1/1994 | WIPO . |
| 95/00535 | 1/1995 | WIPO . |
| 99/17790 | 4/1999 | WIPO . |

OTHER PUBLICATIONS

Sebti et al, "Inhibitors of protein isoprenyl transferases", CA130:25338, 1998.
Int.J. Bio., vol. 23, No. 9, 819–821, 1991.
Bio. Chem. vol. 3876, No. 1, Jan. 1995, Suzuki et al., 523–529.
Life Sci., vol. 48, 1659–1669, Barrett et al, 1995.
Tips, Nov. 1994, vol. 14, Wang et al., 412–419.
Stroke, vol. 24, No. 3, Mar. 1994, Hong et al., 662–668.
Neu. Res., 1995, vol. 17, Aug., Bartus et al., 249–258.
Proc. Natl. Acad. Sci, vol. 93, 3428–3433, Apr. 1996, Saatman et al.
Tet. letts. vol. 29, No. 28, Burkhart et al., 3433–36, 1998.
J. Med Chem, 1993,36, 3472–80, Girish et al.
J. Med Chem., 1994, 37, 2918–29, Harbeson et al.
Synthesis, 1983, No. 8, Aug., 676–678.
J. Med. Chem. 1990, 33, 11–13.
Proc. Natl. Acad. Sci, vol. 92, 7662–7666, Aug. 1995, Edelstein et al.
J. Cir. J., vol. 59, Jan. 1995; Yoshida et al., 40–48.
Neuron, vol. 14, 651–659, Mar. 1995, Higaki et al.
Cytokine, vol. 6, No. 6, Nov. 1994, 597–601, Watanabe et al.
Int.J.Oncology 5: Supp., 1994, 381.
Bio. and Bio. Res. Com. vol. 158, No. 2, 1989, 432–435 McGowan et al.
J. Med. Chem, 1992, 35, 216–220, Angliker et al.
Chem. Letts., 191–194, 1990, Matsueda et al.
TIBS, vol. 16, 1991, 150–153.

*Primary Examiner*—Deborah C. Lambkin
*Attorney, Agent, or Firm*—Keil & Weinkauf

[57] ABSTRACT

The patent describes ketobenzamides of the formula

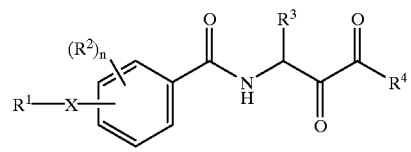

where R1, R2, R3, R4, X and n have the meanings given in the description, and their preparation. The novel compounds are useful for controlling disorders.

4 Claims, No Drawings

KETOBENZAMIDES AS CALPAIN INHIBITORS

This application is a 371 of PCT/EP97/06655 Nov. 28, 1997.

The present invention relates to novel ketobenzamides, to their preparation and to their use in controlling diseases.

Calpains are intracellular, proteolytic enzymes from the cysteine protease group and are found in many cells. Calpains are activated by elevated calcium concentration, with a distinction being made between calpain I or μ-calpain, which is activated by μ-molar concentrations of calcium ions, and calpain II or m-calpain, which is activated by m-molar concentrations of calcium ions (P. Johnson, Int. J. Biochem. 1990, 22(8), 811–22). Further calpain isoenzymes are currently being postulated (K. Suzuki et al., Biol. Chem. Hoppe-Seyler, 1995, 376(9),523–9).

It is assumed that calpains play an important role in various physiological processes. These processes include the cleavage of regulatory proteins such as protein kinase C, cytoskeletal proteins such as MAP 2 and spectrin, and muscle proteins, protein degradation in rheumatoid arthritis, proteins in the activation of platelets, neuropeptide metabolism, proteins in mitosis, and additional examples which are listed in M. J. Barrett et al., Life Sci. 1991, 48, 1659–69 and K. K. Wang et al., Trends in Pharmacol. Sci., 1994, 15, 412–9.

Elevated calpain levels can be measured in various pathophysiological processes, for example: ischemias of the heart (eg. myocardial infarction), the kidney or the central nervous system (eg. stroke), inflammations, muscular dystrophies, cataracts of the eyes, injuries to the central nervous system (eg. trauma), Alzheimer's disease, etc. (see K. K. Wang, above). It is assumed that there is a connection between these diseases and persistently elevated intracellular calcium levels. This results in calcium-dependent processes becoming hyperactivated and no longer being subject to physiological control. A corresponding hyperactivation of calpains can also trigger pathophysiological processes.

For this reason, it was postulated that inhibitors of the calpain enzymes could be of use for treating these diseases. This postulate is confirmed by a variety of investigations. Thus, Seung-Chyul Hong et al., Stroke 1994, 25(3), 663–9 and R. T. Bartus et al., Neurological Res. 1995, 17, 249–58 have demonstrated that calpain inhibitors have a neuroprotective effect in acute neurodegenerative disturbances or ischemias such as occur after cerebral stroke. Following experimental brain traumas, calpain inhibitors improved recovery from the memory performance deficits and neuromotor disturbances which occurred (K. E. Saatman et al. Proc. Natl. Acad. Sci. USA, 1996, 93,3428–3433). C. L. Edelstein et al., Proc.Natl.Acad.Sci. USA, 1995, 92, 7662–6, found that calpain inhibitors have a protective effect on hypoxia-damaged kidneys. Yoshida, Ken Ischi et al., Jap. Circ. J. 1995, 59(1), 40–8 pointed out that calpain inhibitors had favorable effects following cardiac damage which was produced by ischemia or reperfusion. Since calpain inhibitors inhibit the release of the β-AP4 protein, it was suggested that they had a potential use as therapeutic agents in Alzheimer's disease (J. Higaki et al., Neuron, 1995, 14, 651–59). The release of interleukin-1α is also inhibited by calpain inhibitors (N. Watanabe et al., Cytokine 1994, 6(6), 597–601). It has furthermore been found that calpain inhibitors have cytotoxic effects on tumor cells (E. Shiba et al. 20th Meeting Int. Ass. Breast Cancer Res., Sendai J p, Sep. 25–28, 1994, Int. J. Oncol. 5(Suppl.), 1994, 381).

Further possible uses of calpain inhibitors are listed in K. K. Wang, Trends in Pharmacol. Sci., 1994, 15, 412–8.

Calpain inhibitors have already been described in the literature. However, these are predominantly either irreversible inhibitors or peptide inhibitors. As a rule, irreversible inhibitors are alkylating substances and suffer from the disadvantage that they react unselectively in the organism or are unstable. Thus, these inhibitors often exhibit undesirable side-effects, such as toxicity, and as a result are restricted in use or not usable at all. The epoxides E 64 (E. B. McGowan et al., Biochem. Biophys. Res. Commun. 1989, 158, 432–5), α-halo ketones (H. Angliker et al., J. Med. Chem. 1992, 35, 216–20) and disulfides (R. Matsueda et al., Chem. Lett. 1990, 191–194), for example, can be included among the irreversible inhibitors.

Many known reversible inhibitors of cysteine proteases such as calpain are peptide aldehydes, in particular dipeptide or tripepide aldehydes such as Z-Val-Phe-H (MDL 28170) (S. Mehdi, Trends in Biol. Sci. 1991, 16, 150–3) and the compounds from EP 520336. Under physiological conditions, peptide aldehydes frequently suffer from the disadvantage that they are unstable as a result of their high level of reactivity, can be rapidly metabolized and are prone to nonspecific reactions which can be the cause of toxic effects (J. A. Fehrentz and B. Castro, Synthesis 1983, 676–78). Consequently, peptide aldehydes are either of only limited usefulness, or of no use at all, in the treatment of diseases.

The discovery that certain peptide ketone derivatives are also inhibitors of cysteine proteases and calpain, in particular, represents a step forward. Thus, ketone derivatives in which the keto group is activated by an electron-withdrawing group such as $CF_3$ are known to be inhibitors in the case of serine proteases, for example. Derivatives having ketones which are activated by $CF_3$ or similar groups are only slightly effective, or not effective at all, in the case of cysteine proteases (M. R. Angelastro et al., J. Med. Chem. 1990,33, 11–13). Surprisingly, only ketone derivatives in which, on the one hand, α-terminal leaving groups cause an irreversible inhibition and, on the other hand, the keto group is activated by a carboxylic acid derivative, have hitherto been found to be effective inhibitors in the case of calpain (see M. R. Angelastro et al., see above; WO 92/11850; WO 92,12140; WO 94/00095 and WO 95/00535). However, it is only peptide derivatives of these keto amides and keto esters which have hitherto been reported to be effective (Zhao Zhao Li et al., J. Med. Chem. 1993, 36, 3472–80; S. L. Harbenson et al., J. Med. Chem. 1994, 37, 2918–29 and see M. R. Angelastro et al. above).

In addition, ketobenzamides are known from the literature. Thus, the keto ester $PhCO-Abu-COOCH_2CH_3$ has been described in WO 91/09801, WO 94/00095 and 92/11850. However, M. R. Angelastro et al., J. Med. Chem. 1990,33, 11–13 found the analogous phenyl derivative Ph-CONH—CH($CH_2$Ph)—CO—$COOCH_3$ to be only a weak inhibitor of calpain. This derivative is also described in J. P. Burkhardt, Tetrahedron Lett., 1988, 3433–36. However the importance of the substituted benzamides has never been investigated to date.

Substituted, non-peptide ketobenzamide derivatives having an improved effect have now been found.

The present invention relates to ketobenzamides of the formula I

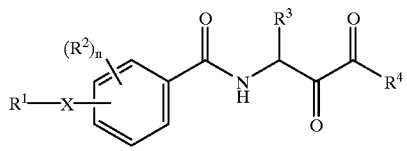

and their tautomeric and isomeric forms, and also, where appropriate, their physiologically tolerated salts, where the variables have the following meanings:

$R^1$ is phenyl, naphthyl, quinolyl, pyridyl, pyrimidyl, pyrazyl, pyridazyl, quinazolyl, quinoxalyl, thienyl, benzothienyl, benzofuryl, benzimidazolyl, furanyl, indolyl, isoquinoline, tetrahydroisoquinoline or tetrahydroquinoline, where the aromatic and heteroaromatic rings can additionally be substituted by one, two or three $R^5$ radicals, $R^2$ is chlorine, bromine, fluorine, $C_1$–$C_6$-alkyl, $C_2$–$C_6$-alkenyl, $C_2$–$C_6$-alkynyl, $C_1$–$C_6$-alkyl-phenyl, $C_2$–$C_6$-alkenyl-phenyl, $C_2$–$C_6$-alkynyl-phenyl, phenyl, NHCO—$C_1$–$C_4$-alkyl, —NHCO-phenyl, —NHCO-naphthyl, $H_2N$—$SO_2$—$C_{1-4}$-alkyl—, COOH, —COO—$C_{1-4}$-alkyl, —CONH—$C_{1-4}$-alkyl, $C_{1-4}$-alkoxy, $NO_2$ or $NH_2$, $R^3$ is $C_1$–$C_6$-alkyl which can also carry a phenyl, cyclopropyl, cyclobutyl, cyclopentyl, cyclohexyl, cycloheptyl, indolyl, pyridyl or naphthyl ring which, for its part, can be substituted by one or two $R^5$ radicals, X is a bond, —$(CH_2)_m$—, —$(CH_2)_m$—O—$(CH_2)_o$—, —$(CH_2)_n$—S—$(CH_2)_m$—, —$(CH_2)_n$—SO—$(CH_2)_m$—, —$(CH_2)_n$—$SO_2$—$(CH_2)_m$—, —CH=CH—, —C≡C—, —CO—CH=CH—, CO—$(CH_2)_m$—, —$(CH_2)_m$—NHCO—$(CH_2)_o$—, —$(CH_2)_m$—CONH—$(CH_2)_o$—, —$(CH_2)_m$—$NHSO_2$—$(CH_2)_o$—, —NH—CO—CH=CH—, —CH=CH—CO—NH—, —$(CH_2)_m$—$SO_2NH$—$(CH_2)_o$— or

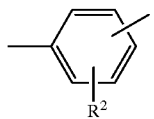

$R^4$ is $OR^6$, $NR^7R^8$,

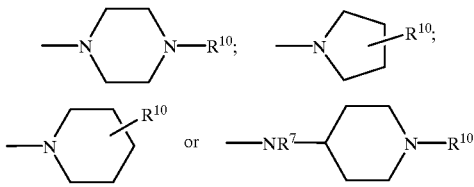

$R^5$ is hydrogen, $C_1$–$C_4$-alkyl, —O—$C_1$–$C_4$-alkyl, OH, Cl, F, Br, I, $CF_3$, $NO_2$, $NH_2$, CN, COOH, COO—$C_1$–$C_4$-alkyl, —NHCO—$C_1$–$C_4$-alkyl, —NHCO-phenyl, —$NHSO_2$—$C_1$–$C_4$-alkyl, —$NHSO_2$-phenyl, —$SO_2$—$C_1$–$C_4$-alkyl or —$SO_2$-phenyl, $R^6$ is hydrogen or $C_1$–$C_6$-alkyl which can be substituted by a phenyl ring which, itself, can also be substituted by one or two $R^9$ radicals, $R^7$ is hydrogen or $C_1$–$C_6$-alkyl, $R^8$ is hydrogen or $C_1$–$C_6$-alkyl which can also be substituted by a phenyl ring, which can carry one or two $R^9$ radicals, or by one of the radicals

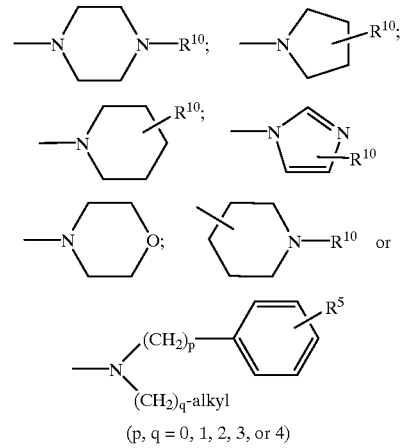

(p, q = 0, 1, 2, 3, or 4)

$R^9$ is hydrogen, $C_1$–$C_4$-alkyl, —O—$C_1$–$C_4$-alkyl, OH, Cl, F, Br, I, $CF_3$, $NO_2$, $NH_2$, CN, COOH, COO—$C_1$–$C_4$-alkyl, —NHCO—$C_1$–$C_4$-alkyl, —NHCO-phenyl, —$NHSO_2$—$C_1$–$C_4$-alkyl, —$NHSO_2$-phenyl, —$SO_2$—$C_1$–$C_4$-alkyl or —$SO_2$-phenyl, $R^{10}$ is hydrogen or $C_1$–$C_6$-alkyl which can be substituted by a phenyl ring which can also be substituted by one or two $R^9$ radicals, n is the number 0, 1 or 2, m is the number 0, 1, 2, 3 or 4, and o is the number 0, 1, 2, 3 or 4.

Preference is given to compounds of the formula I where $R^2$ is hydrogen, $C_1$–$C_4$-alkyl, fluorine or chlorine, $R^3$ is —$CH_2$-phenyl, —$CH_2$-cyclohexyl, n-butanyl or n-pentanyl, each of which can be substituted by an $R^5$ radical, $R^4$ is —$NR^8$, and $R^1$, X and n have the meanings given in claim 1.

The compounds of the formula I can be employed as racemates or as enantiomerically pure compounds or as diastereomers. If enantiomerically pure compounds are desired, these can be obtained, for example, by carrying out a conventional racemate resolution on the compounds of the formula I, or their intermediates, using a suitable optically active base or acid. The enantiomeric compounds may also be prepared by employing commercially obtainable compounds, for example optically active amino acids such as phenylalanine, tryptophan and tyrosine.

The invention also relates to compounds which are mesomeric or tautomeric in relation to compounds of the formula I, for example those compounds in which the keto group of the formula I is present as an enol tautomer.

Some of the novel compounds I can contain a basic or an acidic group. In these cases, the compounds I can be present in the form of their physiologically tolerated salts, which can be obtained by reacting the compounds I with a suitable acid or base.

Examples of suitable acids for forming salts with novel compounds I which contain a basic group are hydrochloric acid, citric acid, tartaric acid, lactic acid, phosphoric acid, methanesulphonic acid, acetic acid, formic acid, maleic acid, fumaric acid, malic acid, succinic acid, malonic acid and sulphuric acid. Examples of suitable bases are potassium hydroxide, sodium hydroxide, lithium hydroxide, triethylamine, α,α,α-tris(hydroxymethyl)methylamine and other amines.

The ketobenzamides I according to the invention can be prepared by different routes, which are outlined in synthesis schemes 1 and 2.

The carboxylic esters II are converted into the acids III using acids or bases, such as hydrochloric acid, lithium hydroxide, sodium hydroxide or potassium hydroxide, in aqueous medium or in mixtures of water and organic solvents, such as alcohols or tetrahydrofuran, at room temperature or at elevated temperatures, such as 25–100° C. The acids III are linked to an α-amino acid derivative using the customary conditions, which are listed, for example, in Houben-Weyl, Methoden der organischen Chemie [Methods of organic chemistry], 4th edition, E5, Ch. V, and C. R. Larock, Comprehensive Organic Transformations, Publisher VCH, 1989, Ch. 9.

The carboxylic acid III is converted into an "activated" acid derivative $R^1$-L, where L is a leaving group such as Cl, imidazole and N-hydroxybenzotriazole, and converted into the derivative IV by reaction with an amino acid derivative $H_2N$—$CHR^3$—COOR. This reaction takes place in anhydrous, inert solvent, such as methylene chloride, tetrahydrofuran and dimethylformamide, at from −20 to +25° C.

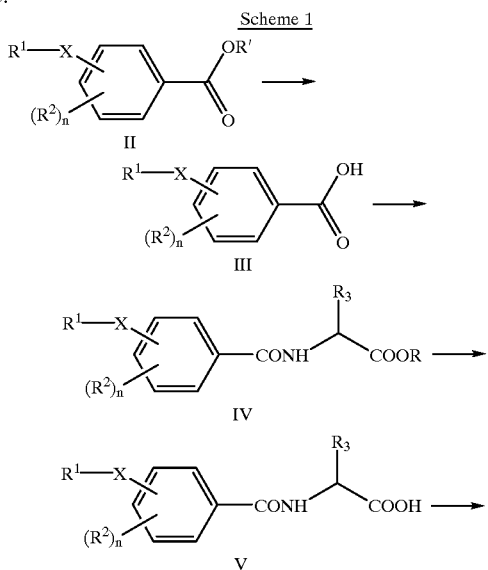

Scheme 1

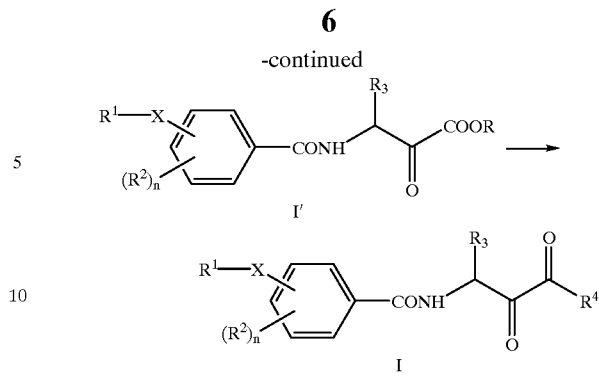

The derivatives IV, which are esters as a rule, are converted into the keto carboxylic acids V in analogy with the hydrolysis described above. The keto esters I' are prepared in a Dakin-West-analogous reaction using a method described by Zhao Zhao Li et al. J. Med. Chem., 1993, 36, 3472–80. In this reaction, a carboxylic acid such as V is reacted, at elevated temperature (50–100° C.) in solvents, such as tetrahydrofuran, with oxalyl chloride monoester and the resulting product is then converted into the keto ester I' according to the invention using bases, such as sodium ethoxide, in ethanol at 25–80° C. The keto esters I' can be hydrolyzed, as described above, to give the keto carboxylic acids according to the invention, for example.

The reaction to give the ketobenzamides I is also carried out in analogy with the method of Zhao Zhao Li et al. (see above). The keto group in I' is protected by adding 1,2-ethanedithiol in association with Lewis acid catalysis, for example using boron trifluoride etherate, in inert solvents, such as methylene chloride, at room temperature, resulting in a dithiane. These derivatives are reacted with amines $R^4$-H in polar solvents, such as alcohols, at temperatures of 0–80° C., resulting in the formation of the keto amides I (eg. $R^4$=$NR^7R^8$).

Scheme II

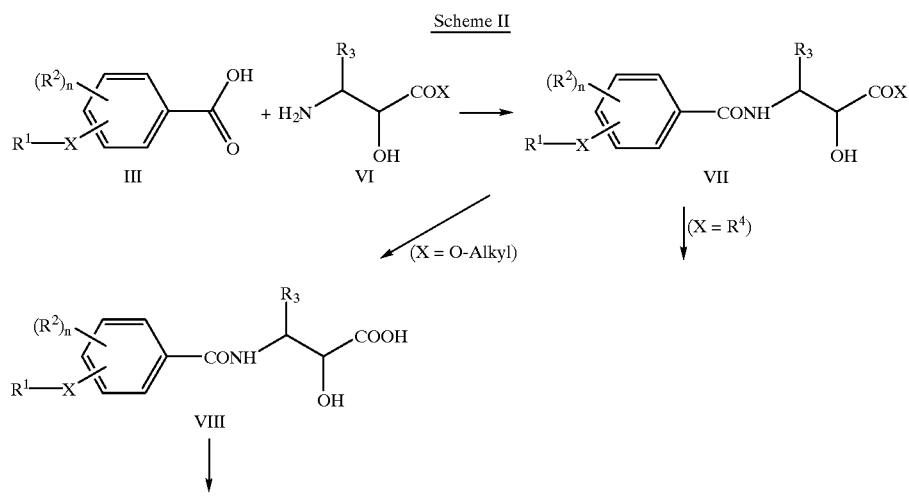

-continued

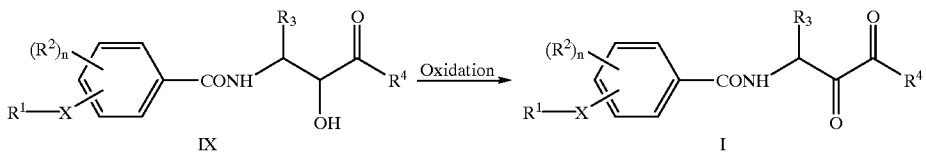

An alternative method is depicted in Scheme 2. The keto carboxylic acids III are reacted with the amino hydroxy carboxylic acid derivatives IV (for preparation of IV, see S. L. Harbenson et al., J. Med. Chem. 1994, 37, 2918–29) using the customary peptide coupling methods (see Houben-Weyl above), resulting in the formation of the amides VII. These alcohol derivatives VII can be oxidized to give the keto carboxylic acid derivatives I according to the invention. A variety of customary oxidation reactions (see C. R. Larock, Comprehensive Organic Transformations, Publisher VCH, 1989, pages 604 f.), such as Swern oxidations and Swern-analogous oxidations, preferably using dimethyl sulfoxide/ pyridine-sulfur trioxide in solvents such as methylene chloride or tetrahydrofuran, with or without the addition of dimethyl sulfoxide, at room temperature or at temperatures of –50 to 25° C., (T. T. Tidwell, Synthesis 1990, 857–70) or sodium hypochloride/TEMPO (S. L. Harbenson et al., see above), can be used for this purpose.

When the compounds VII are a-hydroxy esters (X=O-alkyl), these can be hydrolyzed to give the carboxylic acids VIII in analogy with the above methods, but preferably using lithium hydroxide in water/tetrahydrofuran mixtures at room temperature. Other esters or amides X are prepared by reaction with alcohols or amines under coupling conditions which have already been described. The alcohol derivative X can once again be oxidized to give keto carboxylic acid derivatives I according to the invention.

The synthesis of the carboxylic esters II has already been described in some cases, or can be carried out in accordance with customary chemical methods.

Compounds in which X is a bond are prepared by customary aromatic coupling, for example the Suzuki coupling using boric acid derivatives and halides, while catalyzing with palladium, or the copper-catalyzed coupling of aromatic halides. The alkyl-bridged radicals (X=—(CH$_2$)$_m$—) can be prepared by reducing the analogous ketones or by alkylating the organolithium compounds, for example ortho-phenyloxazolidines, or other organometallic compounds (cf. I. M. Dordor, et al., J. Chem. Soc. Perkin Trans. I, 1984, 1247–52).

Ether-bridged derivatives are prepared by alkylating the corresponding alcohols or phenols using halides.

The sulfoxides and sulfones can be obtained by oxidizing the corresponding thioethers.

Alkene-bridged and alkyne-bridged compounds are prepared, for example, from aromatic halides and corresponding alkenes and alkynes using the Heck reaction (cf. I. Sakamoto et al., Chem. Pharm. Bull., 1986, 34, 2754–59).

The chalcones are produced by the condensation of acetophenones with aldehydes and can, where appropriate, be converted into the analogous alkyl derivatives by means of hydrogenation.

Amides and sulfonamides are prepared from the amines and acid derivatives in analogy with the above-described methods.

The ketobenzamides I according to the invention are inhibitors of cysteine proteases, in particular of cysteine proteases such as calpains I and II and cathepsins B and L.

The inhibitory effect of the ketobenzamides I was ascertained using enzyme tests which are customary in the literature, with the concentration of the inhibitor at which 50% of the enzyme activity is inhibited being determined as the criterion of efficacy. This approach was used to measure the inhibitory effect of the benzamides I on calpain I, calpain II and cathepsin B.

Cathepsin B Test

The inhibition of cathepsin B was determined in analogy with a method described by S. Hasnain et al., J. Biol. Chem. 1993, 268, 235–40.

2 μL of an inhibitor solution, which was prepared from inhibitor and DMSO (final concentrations: 100 μM to 0.01 μM) were added to 88 μL of cathepsin B (human liver cathepsin B (Calbiochem), diluted to 5 units in 500 μM buffer). This mixture is preincubated at room temperature (25° C.) for 60 minutes and the reaction is then started by adding 10 μL of 10 mM Z-Arg—Arg-pNA (in buffer containing 10% DMSO). The reaction is monitored at 405 nm for 30 minutes in a microtiter plate reader. The IC$_{50}$'s are then determined from the maximum slopes.

Calpain I and Calpain II Test

The inhibitory properties of calpain inhibitors are tested in buffer containing 50 mM tris-HCl, pH 7.5; 0.1 M NaCl; 1 mM dithiotreithol [sic]: 0.11 mM CaCl$_2$, using the fluorogenic calpain substrate Suc-Leu-Tyr-AMC (25 mM, dissolved in DMSO, Bachem/Switzerland) (Sasaki et al. J. Biol. Chem. 1984, Vol. 259, 12489–12494). Human μ-calpain is isolated from erythrocytes following the methods of Croall and DeMartino (BBA 1984, Vol. 788, 348–355) and Graybill et al. (Bioorg. & Med. Lett. 1995, Vol. 5, 387–392). After several chromatographic steps (DEAE Sepharose, phenyl Sepharose, Superdex 200 and Blue Sepharose), the enzyme is obtained at a purity of <95%, as assessed by SDS-PAGE, Western blot analysis and N-terminal sequencing. The fluorescence of the cleavage product 7-amino-4-methylcoumarin (AMC) is followed in a Spex-Fluorolog fluorimeter at $\lambda_{ex}$=380 nm and $\lambda_{em}$=460 nm. When the experiments are carried out at temperatures of 12° C., the cleavage of the substrate is linear, and the autocatalytic activity of calpain is low, over a measurement period of 60 min (see Chatterjee et al. 1996, Bioorg. & Med. Chem. Lett., Vol. 6, 1619–1622). The inhibitors and the calpain substrate are added to the experimental mixture as DMSO solutions, in which the final concentration of DMSO should not exceed 2%.

In a typical experimental mixture, 10 μl of substrate (250 μm final concentration) and then 10 μl of μ-calpain (2 μg/ml final concentration, ie. 18 nM) are added to a 1 ml cuvette which contains buffer. The calpain-mediated cleavage of the substrate is measured for from 15 to 20 min. 10 μl of inhibitor (50 or 100 μM solution in DMSO) are then added and inhibition of the cleavage is measured for a further 40 min. K$_i$ values are determined using the customary equation for reversible inhibition, ie. K: l(v$_o$/v)–1 [sic]; where I=inhibitor concentration, v$_o$=initial velocity before adding the inhibitor; v$_i$=reaction velocity at equilibrium.

The K$_I$ for (S)-N(1-ethoxycarbonyl-1-oxo-3-phenyl-2-propanyl)-2-phenylbenzamide (Example 24) was found to be <10 μM. This derivative is therefore markedly more effective than is the very closely related N(1-ethoxycarbonyl-1-oxo-3-phenylpropan-2-yl)-benzamide (from M. R. Angelastro et al., J. Med. Chem. 1990, 33, 11–13).

Calpain is an intracellular cysteine protease. Calpain inhibitors have to be able to pass through the cell membrane in order to prevent degradation by calpain of intracellular proteins. Some known calpain inhibitors, such as E 64 and leupeptin, are only able to pass through cell membranes with difficulty and consequently only have a poor effect in cells even though they are good inhibitors of calpain. The aim is to find compounds which are better able to traverse membranes. Human platelets were used for demonstrating the membrane-traversing ability of calpain inhibitors.

Calpain-mediated Degradation of Tyrosine Kinase pp60src in Platelets

The tyrosine kinase pp60src was cleaved by calpain after platelets had been activated. This was investigated in detail by Oda et al. in J. Biol. Chem., 1993, Vol 268, 12603–12608. This study demonstrated that the cleavage of pp60src can be prevented by calpeptin, which is an inhibitor of calpain. The cellular efficacy of the novel substances was tested in accordance with this publication. Fresh human, citrate-treated blood was centrifuged at 200 g for 15 min. The platelet-rich plasma was pooled and diluted 1:1 with platelet buffer (platelet buffer: 68 mM NaCl, 2.7 mM KCl, 0.5 mM $MgCl_2 \times 6\ H_2O$, 0.24 mM $NaH_2PO_4 \times H_2O$, 12 mM $NaHCO_3$, 5.6 mM glucose, 1 mM EDTA, pH 7.4). After a centrifugation and washing step using platelet buffer, the platelets were adjusted to $10^7$ cells/ml. The human platelets were isolated at RT.

In the test mixture, isolated platelets ($2 \times 10^6$) were preincubated, at 37° C. for 5 min, with different concentrations of inhibitors (dissolved in DMSO). The platelets were then activated with 1 $\mu$M ionophore A23187 and 5 mM $CaCl_2$. After an incubation of 5 min, the platelets were centrifuged briefly at 13,000 rpm and the pellet was taken up in SDS sample buffer (SDS sample buffer: 20 mM tris-HCl, 5 mM EDTA, 5 mM EGTA, 1 mM DTT, 0.5 mM PMSF, 5 $\mu$g/ml leupeptin, 10 $\mu$m pepstatin, 10% glycerol and 1% SDS). The proteins were fractionated in a 12% gel, and pp60src and its 52 kDa and 47 kDa cleavage products were identified by Western blotting. The polyclonal rabbit anti-Cys-src ($pp60^{c-src}$) antibody employed was obtained from Biomol Feinchemikalien (Hamburg). This primary antibody was detected using a goat HRP-coupled second antibody (Boehringer Mannheim, FRG). The Western blotting was carried out in accordance with known methods.

The cleavage of pp60src was quantified densitometrically, with use being made, as controls, of non-activated platelets (control 1: no cleavage) and platelets which were treated with ionophore and calcium (control 2: corresponds to 100% cleavage). The $ED_{50}$ value corresponds to the concentration of inhibitor at which the intensity of the color reaction of the 60 kDa band corresponds to the value: intensity of control 1 plus control 2 divided by 2.

Glutamate-induced Cell Death in Cortical Neurones

The test was carried out as described in Choi D. W., Maulucci-Gedde M. A. and Kriegstein A. R., "Glutamate neurotoxicity in cortical cell culture". J. Neurosci. 1989, 7, 357–368.

Cortex halves are dissected out from 15-day mouse embryos and the individual cells are isolated enzymically (trypsin). These cells (glia and cortical neurones) are sown in 24-well plates. After three days (laminin-coated plates) or seven days (ornithine-coated plates), mitosis treatment is carried out using FDU (5-fluoro-2-deoxyuridine). At 15 days after preparing the cells, cell death is induced by adding glutamate (15 minutes). The calpain inhibitors are then added after removing the glutamate. 24 hours later, cell damage is ascertained by determining lactate dehydrogenase (LDH) in the cell culture supernatant.

It is postulated that calpain also plays a role in apoptotic cell death (M. K. T. Squier et al. J. Cell. Physiol. 1994, 159, 229–237; T. Patel et al. Faseb Journal 1996, 590, 587–597). For this reason, cell death was induced with calcium in the presence of a calcium ionophore in another model, ie. a human cell line. Calpain inhibitors have to get into the cell, and there inhibit calpain, in order to prevent the cell death which has been induced.

Calcium-mediated Cell Death in NT2 Cells

In the human cell line NT2, cell death is induced by calcium in the presence of the ionophore A 23187. 20 hours before the experiment, cells are plated out in microtiter plates at the rate of $10^5$ cells/well. Once the 20 hours have elapsed, the cells are incubated with different concentrations of inhibitors in the presence of 2.5 $\mu$M ionophore and 5 mM calcium. After 5 hours, 0.05 ml of XTT (Cell Proliferation Kit II, Boehringer Mannheim) is added to each reaction mixture. The optical density is determined approximately 17 hours later, in accordance with the manufacturer's instructions, in an SLT EASY READER EAR 400. The optical density at which half the cells have died is computed from the two measurements without inhibitors, which were incubated [sic] in the absence and presence of ionophore. The concentration of the inhibitor which achieves this half-maximum optical density is the $IC_{50}$ value.

An increase in glutamate activity, which leads to states of super excitation or toxic effects in the central nervous system (CNS), occurs in a number of neurological diseases or psychic disorders.

Consequently, substances which inhibit glutamate-mediated effects can be used to treat these diseases. Glutamate antagonists, which also include, in particular, NMDA antagonists or their modulators and the AMPA antagonists, are suitable for therapeutic use as agents against neurodegenerative diseases (Huntington's chorea and Parkinson's diseases), neurotoxic disturbances following hypoxia, anoxia or ischaemia, as occur following a stroke, or as antiepileptics, antidepressives and anxiolytics (cf. Arzneim. Forschung 1990, 40, 511–514; TIPS, 1990, 11, 334–338 and Drugs of the Future 1989, 14 (11), 1059–1071).

Intracerebral administration of excitatory amino acids (EAA) induces a superexcitation which is so massive that it rapidly leads to convulsions and the death of the animals. These symptoms can be inhibited by the systemic, eg. intraperitoneal, administration of centrally acting EAA antagonists. Since excessive activation of EAA receptors in the central nervous system plays an important role in the pathogenesis of various neurological diseases, it can be concluded that substances which are demonstrated to exhibit EAA antagonism in vivo will be useful in the therapy of CNS diseases of this nature. These diseases include, inter alia, focal and global ischaemias, trauma, epilepsies and various neurodegenerative diseases, such as Huntington's chorea, Parkinson's disease, inter alia.

It has already been shown that calpain inhibitors, too, exhibit a protective effect against EAA-induced cell death in cell cultures (H. Cauer et al., Brain Research 1993, 607, 354–356; Yu Cheg and A. Y. Sun, Neurochem. Res. 1994, 19, 1557–1564). Surprisingly, the calpain inhibitors which are included in this application are effective even against the convulsions which are induced by EAA (eg. NMDA or AMPA) and consequently point to a therapeutic use in the abovementioned CNS diseases.

The ketobenzamides I are inhibitors of cysteine derivatives such as calpain I and/or II and cathepsin B and/or L and may consequently be used for controlling disorders which are associated with increased activity of the calpain or cathepsin enzymes. They are therefore useful for treating neurodegenerative disorders which occur following ischemia, trauma, subarachnoid hemorrhage and stroke, and which include, in particular, cerebral stroke and cranial trauma, for treating neurodegenerative disorders such as multi-infarct dementia, Alzheimer's disease and Huntington's disease and, furthermore, for treating damage to the heart following cardiac ischemias, damage to the kidneys following renal ischemias, skeletal muscle damage, muscular dystrophies, damage which arises due to the proliferation of the smooth muscle cells, coronary vasospasms, cerebral vasospasms, cataracts of the eyes and restenosis of blood vessels following angioplasty. Furthermore, the benzamides I can be of use for the chemotherapy of tumors and their metastases and for treating disorders in which there is an elevated level of interleukin 1, as in inflammations and rheumatic diseases. In addition to the customary drug auxiliary substances, the drug preparations according to the invention also comprise a therapeutically effective quantity of the compounds I.

For local external use, for example in powders, ointments or sprays, the active compounds can be present in the customary concentrations. As a rule, the active compounds are present in a quantity of from 0.001 to 1% by weight, preferably of from 0.01 to 0.1% by weight.

For internal use, the preparations are administered in single doses. In a single dose, from 0.1 to 100 mg are administered per kg of body weight. The preparation can be administered daily in one or more dosages depending on the nature and severity of the diseases.

The drug preparations according to the invention comprise, in addition to the active compound, the customary carriers and diluents in accordance with the desired mode of administration. Pharmaceutical auxiliary substances, such as ethanol, isopropanol, ethoxylated castor oil, ethoxylated hydrogenated castor oil, polyacrylic acid, polyethylene glycol, polyethylene glycostearate, ethoxylated fatty alcohols, paraffin oil, yellow soft paraffin and wool fat can be used for local external applications. Lactose, propylene glycol, ethanol, starch, talc and polyvinylpyrrolidone, for example, are useful for internal applications.

Furthermore, antioxidants, such as tocopherol and butylated hydroxyanisole, and also butylated hydroxytoluene, taste-improving additives, stabilizers, emulsifiers and glidants can also be present.

These substances which are present in the preparation in addition to the active compound, and also the substances which are used in producing the pharmaceutical preparations, are toxicologically harmless and compatible with the relevant active compound. The drug preparations are produced in a customary manner, for example by mixing the active compound with other customary carriers and diluents.

The drug preparations can be administered in various ways, for example perorally, parenterally, such as intravenously by infusion, subcutaneously, intraperitoneally and topically. Thus, possible preparation forms are tablets, emulsions, infusion solutions, injection solutions, pastes, ointments, gels, creams, lotions, powders and sprays.

EXAMPLES

Example 1

(S)-2-(E-2-(Naphth-2-yl)-ethen-1-yl)-N-(1-(N-(3-morpholino-1-yl-propan-1-yl)carbamoyl-1-oxo-3-phenylpropan-2-yl)benzamide

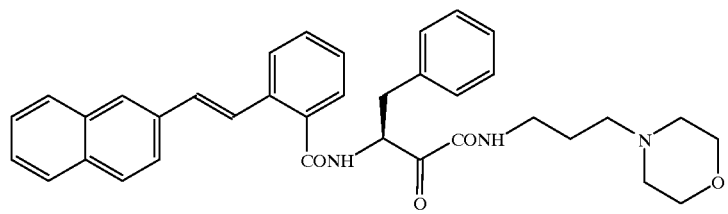

a) Ethyl 2-(2-(E-naphth-2-yl)ethen-1-yl)benzoate 29.7 g (0.13 mol) of 2-vinylnaphthalene, 25 g (0.16 mol) of ethyl 2-bromobenzoate, 22.5 ml (0.16 mol) of triethylamine, 0.54 g of palladium diacetate and 1.44 g of triphenylphosphine were heated at 100° C. for 20 h in 200 ml of acetonitrile. After that, the whole was poured onto water and this mixture was extracted several times with ethyl acetate. The organic phase was concentrated under reduced pressure and the residue was purified by chromatography on silica gel. Yield: 34g (71%).

b) 2-(E-2-(Naphth-2-yl)ethen-1-yl)benzoic acid 34 g (112.5 mmol) of the intermediate la were dissolved in 200 ml of tetrahydrofuran, and 9.5 g (168.7 mmol) of 80% strength potassium hydroxide, dissolved in 150 ml of water, were added to this solution. The whole was refluxed for 10 h.

The reaction mixture was then acidified with concentrated hydrochloric acid and extracted with ethyl acetate. The organic phase was washed with water, dried and concentrated under reduced pressure. The residue was treated with a further small quantity of ethyl acetate and filtered off with suction. Yield 23.8 g (78%).

(S)-O-(tert-Butyl)-N-(1-(N-(3-morpholino-1-ylpropan-1-yl)-carbamoyl-3-phenylpropan-1-ol-2-yl)carbamate 1.6 g (10 mmol) of diethyl cyanophosphate and 1.0 g (10 mmol) of triethylamine are added consecutively, at −5° C., to 2.95 g (10 mmol) of O-(tert-butyl) 2-(S)-N-(1-carboxy-2-hydroxy-3-phenylpropan-1-ol-2-yl)-carbamate (S. L. Harbeson et al., J. Med. Chem. 1994, 37, 2918–29) and 1.4 g (10 mmol) of N-(3-aminopropan-1-yl)morpholine in 50 ml of anhydrous dimethylformamide. The whole was stirred at −5° C. for 1 h and then at room temperature for 16 h. It was then poured onto water and this mixture was extracted with ethyl acetate. The organic phase was extracted with aqueous citric acid solution. This aqueous phase was then rendered alkaline with dilute sodium hydroxide solution and extracted with ethyl acetate. The organic phase was dried and concentrated under reduced pressure, with 2.3 g (55%) of product being obtained.

3-(S)-3-Amino-2-hydroxy-3-phenyl-N-(3-morpholin-1-ylpropan-1-yl)butyramide 2.1 g (5 mmol) of the intermediate 1c were dissolved in 60 ml of methylene chloride, and 60 ml of trifluoroacetic acid were added to this solution. The mixture was stirred at room temperature for 30 min. After that, it was concentrated under reduced pressure and the residue was dissolved in, and reprecipitated from, methylene chloride/ether. 2.4 g of crude product were obtained.

e) 2-(S)-2-(E-2-(Naphth-2-yl)ethen-1-yl)-N-(1-(N-(3-morpholino-1-ylpropan-1-yl)carbamoyl)-1-hydroxy-3-phenylpropan-2-yl)-benzamide 0.65 g (4 mmol) of diethyl cyanophosphate and 0.8 g (8 mmol) of triethylamine were added consecutively, at −5° C., to 2.4 g (4 mmol) of the intermediate 1d and 1.1 g (4 mmol) of the intermediate 1b in 30 ml of anhydrous dimethylformamide. The whole was then stirred at −5° C. for 1 h and at room temperature for a further 16 h. After that, 200 ml of water were added and this mixture was extracted with diethyl ether.

The aqueous phase was neutralized with dilute sodium hydroxide solution and then extracted with ethyl acetate. This organic phase was dried and concentrated under reduced pressure. The residue was recrystallized from ethyl acetate. Yield: 0.8g (35%).

f) 2-(S)-2-(E-2-(Naphth-2-yl)ethen-1-yl)-N-(1-(N-(3-morpholino-1-ylpropan-1-yl)carbamoyl)-1-oxo-3-phenylpropan-2-yl)benzamide 0.38 g (2.4 mmol) of pyridine/sulfur trioxide complex, dissolved in 4 ml of dimethyl sulfoxide, was added, at room temperature, to 0.46 g (0.8 mmol) of the intermediate 1e and 0.3 g (3.2 mmol) of triethylamine in 8 ml of dimethyl sulfoxide. The whole was stirred for 16 h. After that, the mixture was first of all diluted with water and then extracted with methylene chloride. The organic phase was dried and concentrated under reduced pressure. The residue was treated with ether, with 0.3 g (65%) of product resulting.

1H NMR (CDCl$_3$): δ=1.7(2H), 2.4(6H), 3.2(1H), 3.5(3H), 3.7(4H), 5.8(1H), 6.5(1H), 7.0–8.0(19H) and 8.8(1H) ppm.

Example 2

(S)-2-(E-2-Naphth-2-yl)ethen-1-yl)-N-(1-carbamoyl-1-oxo-3-phenylpropan-2-yl)benzamide [sic]

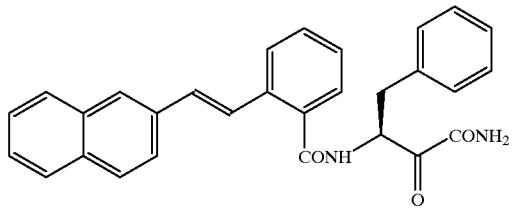

a) 2-(S)-O-(tert-Butyl)-N-(1-carbamoyl-3-phenylpropan-1-ol-2-yl)carbamate 217.7 g (60 mmol) of O-(tert-butyl) 2-(S)-N-(1-carboxy-2-hydroxy-3-phenylpropan-1-ol-2-yl)carbamate (S. L. Harbeson et al., J. Med. Chem. 1994, 37, 2918–29) were reacted with ethanolic ammonia solution in analogy with Example 1c. Yield: 13.5 g (76%).

b) 3-(S)-3-Amino-2-hydroxy-3-phenylbutyramide 13.4 g (45.5 mmol) of the intermediate compound 2a were reacted in analogy with Example 1d. 12.3 g (88%) of product were obtained.

c) 2-(S)-2-(E-2-(Naphth-2-yl)ethen-1-yl)-N-(1-carbamoyl-1-hydroxy-3-phenylprop-2-yl)benzamide 1.26 g (6.6 mmol) of N'-(3-dimethylaminopropyl)-N-ethylcarbodiimide hydrochloride (EDC), 1.85 g (6 mmol) of the intermediate compound 1b and 1.2 g (12 mmol) of N-methylmorpholine were added consecutively, at −5° C., to 1.65 g (6 mmol) of the intermediate compound 2b and 0.81 g (6 mmol) of 1-hydroxybenzotriazole (HOBT) in 10 ml of anhydrous dimethylformamide. After that, the whole was stirred at −5° C. for 1 h and then at room temperature for a further 16 h. Water was subsequently added and the precipitate was filtered off with suction. Yield: 1.3 g (48%) of product.

d) (S)-2-(2-(Naphth-2-yl)ethen-1-yl)-N-(1-carbamoyl-1-oxo-3-phenylpropan-2-yl)benzamide 0.45 g (1 mmol) of the intermediate compound 2c was oxidized in analogy with Example 1f. Yield: 0.28 g (62%). MS: m/e=458(M$^+$).

Example 3

2-(S)-2-(E-2-(3,4-Dimethoxyphenyl)ethen-1-yl)-N-(1-carbamoyl-1-oxo-3-phenylpropan-2-yl)benzamide

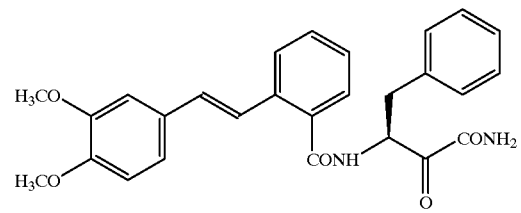

a) Ethyl 2-(E-2-(3,4-dimethoxyphenyl)ethen-1-yl)benzoate 5 g (30.5 mmol) of 3,4-dimethoxystyrene were reacted with ethyl 2-bromobenzoate in dimethylformamide at 120° C. in analogy with Example 1a. 7.2 g (94%) of product were obtained.

b) 2-(E-2-(3,4-Dimethoxyphenyl)ethen-1-yl)benzoic acid 7 g (22 mmol) of the intermediate 3a were hydrolyzed with 4M sodium hydroxide solution in analogy with Example 1b. Yield: 6.2 g (98%).

c) 2-(S)-2-(2-(3,4-Dimethoxyphenyl)ethen-1-yl)-N-(1-carbamoyl-1-hydroxy-3-phenylpropan-2-yl)benzamide 1.7 g (6 mmol) of the intermediate compound 2b were reacted with the compound 3b in analogy with Example 2c. Yield: 2.1 g (76%).

d) 2-(S)-2-(E-2-(3,4-Dimethoxyphenyl)ethen-1-yl)-N-(1-carbamoyl-1-oxo-3-phenylpropan-2-yl)benzamide 0.45 g (1 mmol) of the intermediate compound 3c was oxidized in analogy with Example 1f. 0.28 g (62%) of product was obtained.

MS: m/e=479(M$^+$).

Example 4

(S)-4-(2-Naphthylamido)methyl-N-(1-carbamoyl-1-oxo-3-phenylpropan-2-yl)benzamide

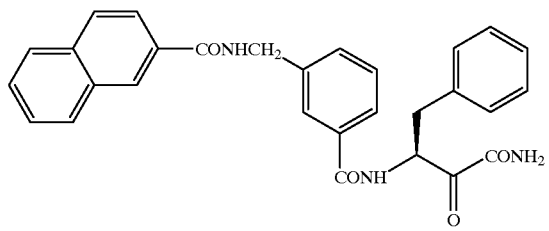

a) 4-(2-Naphthylamido)methylbenzoic acid 12.6 g (66.2 mmol) of 2-naphthoyl chloride, dissolved in 150 ml of tetrahydrofuran, were added dropwise, at 10° C., to 10 g (66.2 mmol) of 4-aminomethylbenzoic acid in 150 ml of pyridine. The whole was then stirred at room temperature for 16 h. The mixture was concentrated under reduced pressure and the resulting residue was purified by chromatography (mobile solvent: methylene chloride/methanol=10/1), with 11.3 g (56%) of product resulting.

b) 4-(2-Naphthylamido)methyl-N-(3-(S)-1-carbamoyl-1-hydroxy-3-phenylpropan-2-yl)benzamide 1.2 g (4 mmol) of the intermediate 4a were reacted with 3-(S)-3-amino-2-hydroxy-3-phenylbutyramide 2b in analogy with Example 2c, with 1.7 g (88%) of product resulting.

c) (S)-4-(2-Naphthylamido)methyl-N-(1-carbamoyl-1-oxo-3-phenylpropan-2-yl)benzamide 0.48 g (1 mmol) of the intermediate compound 4b was oxidized in analogy with Example 1f. Yield: 0.31 g (65%).

1H NMR ($D_6$-DMSO): δ=2.9(1H), 3.2(1H), 4.5(2H), 5.2 (1H), 7.0–8.0(16H), 8.2(1H), 8.7(1H) and 9.1(2H) ppm.

Example 5

(S)-2-Phenyl-N-(1-carbamoyl-1-oxo-3-phenylpropan-2-yl)benzamide

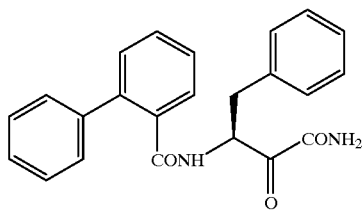

a) 2-Phenyl-N-(3-(S)-1-carbamoyl-1-hydroxy-3-phenylpropan-2-yl)-benzamide 0.8 g (4 mmol) of 2-biphenylcarboxylic acid and 1.2 g (4 mmol) of intermediate compound 2b were reacted in analogy with Example 2c. Yield: 1.2 g (80%).

b) (S)-2-Phenyl-N-(1-carbamoyl-1-oxo-3-phenylpropan-2-yl)-benzamide 0.75 g (2 mmol) of the intermediate compound 5a was oxidized in analogy with Example 1f. Yield: 0.35 g (47%).

1H NMR ($D_6$-DMSO): δ=2.8(1H), 3.1(1H), 5.2(1H), 7.0–7.5(14H), 7.9(1H), 8.1(1H) and 8.9(1H) ppm.

Example 6

(S)-2-(Naphth-2-ylmethyl)-N-(1-carbamoyl-1-oxo-3-phenylpropan-2-yl)benzamide

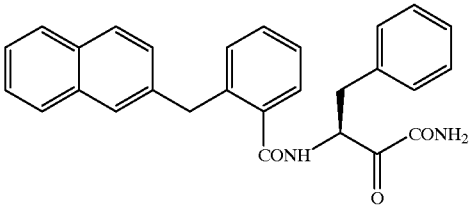

a) 4,4-Dimethyl-2-(2-(naphth-2-ylhydroxymethyl)phenyl)-2-oxazoline 104 ml of a 1.6M butyllithium solution were slowly added dropwise, at −78° C., to 25 g (0.14 mol) of 4,4-dimethyl-2-phenyl-2-oxazoline and 0.1 g of triphenylmethane in 400 ml of anhydrous tetrahydrofuran. The whole was stirred for 1 h. After that, the mixture was allowed to warm to −30° and a solution of 20.3 g (0.13 mol) of 2-naphthaldehyde, dissolved in 200 ml of anhydrous tetrahydrofuran, was added dropwise. The mixture was stirred at from −20 to −30° C. for a further 1 h. The reaction solution was then allowed to warm to room temperature and the solvent was removed under reduced pressure. The residue was added to ice water, with this mixture subsequently being extracted with ether. The organic phase was dried and concentrated under reduced pressure. The residue was purified by chromatography (mobile solvent: n-heptane/acetone=40/3). Yield: 25.3 g (54%).

b) 3-Napth-2-ylphthalide 22 g (66 mmol) of the intermediate 6a were boiled under reflux for 2 h in a mixture of 250 ml of ethanol and 100 ml of 1M hydrochloric acid. After that, the ethanol was removed under reduced pressure and the resulting precipitate was filtered off with suction. Yield: 16.4 g (95%).

c) 2-Naphth-2-ylbenzoic acid 16 g (61.5 mmol) of the intermediate 6b were dissolved in a mixture of 100 ml of tetrahydrofuran and 250 ml of ethanol and then hydrogenated after 5 g of palladium/barium sulfate had been added. After that, the whole was filtered and the filtrate was concentrated under reduced pressure. The residue was recrystallized in toluene, with 13.6 g (85%) of product resulting.

d) 2-(Naphth-2-yl)methyl-N-(-3-(S)-1-carbamoyl-1-hydroxy-3-phenylpropan-2-yl)benzamide 1.05 g (4 mmol) of the intermediate 6c were reacted with the intermediate 2b in analogy with Example 2c, with 1.7 g (97%) of the product resulting.

e) (S)-2-(Naphth-2-yl)methyl-N-(1-carbamoyl--oxo-3-phenylpropan-2-yl)benzamide 0.88 g (2 mmol) of the intermediate compound 6d was oxidized in analogy with Example 1f. Yield: 0.52 g (60%).

1H NMR ($D_6$-DMSO): δ=2.8(1H), 3.2(1H), 4.1(2H), 5.3 (1H), 7.1–8.0(17H), 8.1(1H) and 8.9(1H) ppm.

Example 7

(S)-3-(2-Naphthyl)sulfonamido-N-(1-carbamoyl-1-oxo-3-phenylpropan-2-yl)benzamide

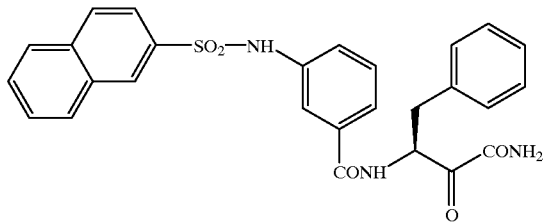

a) Ethyl 3-(2-naphthylsulfonamido)benzoate 34.3 g (0.15 mol) of 2-napthalenesulfonyl chloride, dissolved in 250 ml of tetrahydrofuran, are added dropwise, at 0° C., to 25 g (0.15 mol) of ethyl 3-aminobenzoate and 63 ml (0.45 mol) of triethylamine in 400 ml of tetrahydrofuran. After that, the whole is refluxed for 1 h. The organic solvent was removed under reduced pressure and the residue was partitioned between ethyl acetate and water. The ethyl acetate phase was dried and concentrated under reduced pressure. Yield: 55 g (100%).

b) 3-(2-Naphthylsulfonamido)benzoic acid 55 g (0.15 mol) of the intermediate compound 7a were dissolved in 400 ml of tetrahydrofuran, and 400 ml of 4M sodium hydroxide solution were added. The whole was stirred at 60° C. for 1.5 h. The organic solvent was removed under reduced pressure. The remaining aqueous phase was stirred into dilute hydrochloric acid. The resulting precipitate was dissolved in ethyl acetate, and this solution was washed with water, dried and concentrated under reduced pressure. The residue was then treated with methylene chloride. After that, 37.3 g (75%) of product were obtained.

c) 3-(2-Naphthyl)sulfonamido-N-(-3-(S)-1-carbamoyl-1-hydroxy-3-phenylpropan-2-yl)benzamide 0.55 g (1.68 mmol) of the intermediate compound 7b was reacted with the compound 2b in analogy with example 2c. Yield: 0.72 g (86%).

d) (S)-3-(2-Naphthyl)sulfonamido-N-(1-carbamoyl-1-oxo-3-phenylpropan-2-yl)benzamide 0.7 g (1.4 mmol) of the intermediate compound 7c was oxidized in analogy with Example 1f. Yield: 0.68 g (98%).

1H NMR (D$_6$-DMSO): δ=2.9(1H), 3.1(1H), 5.2(1H), 7.0–8.1(17H), 8.2(1H), 8.8(1H) and 10.5(1H) ppm.

Example 8

(S)-3-(2-Naphthyl)sulfonamido-N-(1-N-(3-(imidazol-1-ylpropan-1-yl)carbamoyl-1-oxo-3-phenylpropan-2-yl)benzamide a) Ethyl 3-(S)-3-amino-2-hydroxy-4-phenylbutyrate 28 g (0.12 mol) of 3-(S)-3-amino-2-hydroxy-4-phenylbutyric acid (S. L. Harbeson et al., J. Med. Chem. 1994, 37, 2918–29) were boiled under reflux for 3 h in 500 ml of a 1M ethanolic solution of hydrogen chloride. After that, the whole was concentrated under reduced pressure and the residue was partitioned between water and ethyl acetate. The ethyl acetate phase was rendered alkaline with aqueous sodium hydrogen carbonate solution, in association with which an oil was separated out. This oil was taken up in ethyl acetate and this solution was dried and concentrated under reduced pressure. Yield: 18 g.

b) 3-(Naphth-2-yl)sulfonamido-N-(2-(S)-1-ethoxycarbonyl-1-hydroxy-3-phenylpropan-2-yl)benzamide 16.5 g (50.4 mmol) of the intermediate compound 7b and 11.2 g (50.4 mmol) of the compound 8a were reacted in analogy with Example 2c. Yield: 7.8 g (30%).

c) 3-(2-Naphthyl)sulfonamido-N-(2-(S)-1-carboxy-1-hydroxy-3-phenylpropan-2-yl)benzamide 7.8 g (14.6 mmol) of the intermediate compound 8b were dissolved in 150 ml of tetrahydrofuran, and 1.1 g (44 mmol) of lithium hydroxide, dissolved in 20 ml of water, were added. The whole was stirred at room temperature for 1 h. After that, the organic solvent was removed under reduced pressure and the aqueous phase was rendered weakly acidic using 1M hydrochloric acid. The resulting precipitate was filtered off with suction. Yield: 7.2 g (98%).

d) 3-(Naphth-2-yl)sulfonamido-N-(2-(S)-1-N-(3-(imidazol-1)-ylpropan-1-yl)carbamoyl-1-hydroxy-3-phenylpropan-2-yl)-benzamide 1 g (2 mmol) of the intermediate compound 8c was reacted with 3-aminopropan-1-yl-1-imidazole in analogy with Example 2c. Yield: 0.63 g (53%).

e) (S)-3-(2-Naphthyl)sulfonamido-N-(1-N-(3-(imidazol-1-ylpropan-1-yl)carbamoyl-1-oxo-3-phenylpropan-2-yl)benzamide 0.6 g (0.98 mmol) of the intermediate compound 8d was oxidized in analogy with Example 1f, with 0.55 g (92%) of product resulting.

Example 9

(S)-N-(1-N-(N-Benzylpiperidin-4-yl)carbamoyl-1-oxo-3-phenylpropan-2-yl)-3-(naphth-2-yl)sulfonamido)benzamide

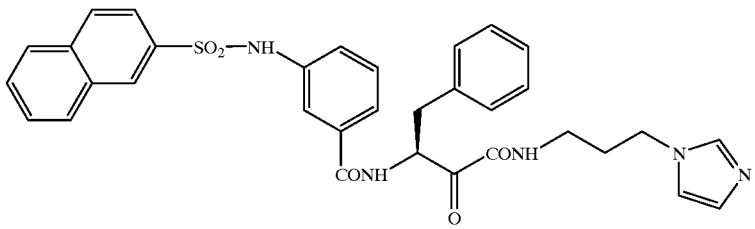

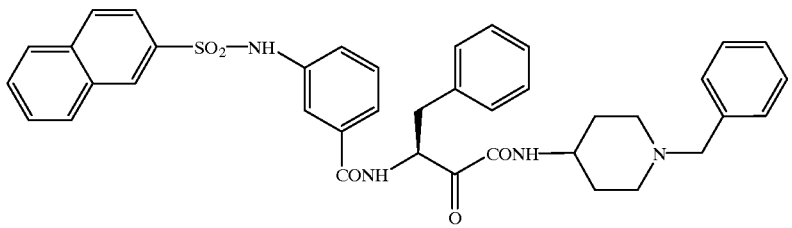

a) N-(2-(S)-1-N-(N-Benzylpiperidin-4-yl)carbamoyl-1-hydroxy-3-phenylpropan-2-yl)-3-(naphth-2-yl)sulfonamidobenzamide 1 g (2 mmol) of the intermediate compound 8c and 4-amino-N-benzylpiperidine were reacted in analogy with Example 2c, with 0.67 g (50%) of product resulting.

b) (S)-N-(1-N-(N-Benzylpiperidin-4-yl)carbamoyl-1-oxo-3-phenylpropan-2-yl)-3-(naphth-2-yl)sulfonamido)benzamide 0.65 g (1 mmol) of the intermediate compound 9a was oxidized in analogy with Example 1f, with 0.59 g (91%) of product resulting.

Example 10

(S)-2-(E-2-(3,4-Dimethoxyphenyl)ethen-1-yl)-N-(1-N-(3-morpholino-1-ylpropan-1-yl)carbamoyl)-1-oxo-3-phenylpropan-2-yl)benzamide

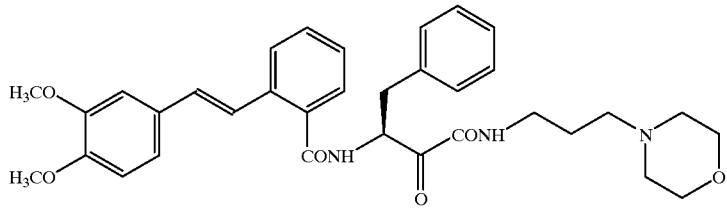

a) 2-(E-2-(3,4-Dimethoxyphenyl)ethen-1-yl)-N-(2-(S)-1-N-(3-morpholino-1-ylpropan-1-yl)carbamoyl)-1-hydroxy-3-phenylpropan-2-yl)benzamide 1.7 g (6 mmol) of the intermediate compound 3b were reacted with the compound 2b in analogy with Example 2c. Yield: 1.2 g (34%).

b) (S)-2-(E-2-(3,4-Dimethoxyphenyl)ethen-1-yl)-N-(1-N-(3-morpholino-1-ylpropan-1-yl)carbamoyl)-1-oxo-3-phenylpropan-2-yl)benzamide 0.6 g (1 mmol) of the intermediate compound was oxidized in analogy with Example 1f. Yield: 0.12 g (20%).

1H NMR (CDCl$_3$): δ=1.8(2H), 2.4–2.7(6H), 3.1(1H), 3.5(2H), 3.6–3.8(5H), 3.9(6H), 5.7(1H), 6.3(1H), 6.8–7.9(14H) and 8.5(1H) ppm.

Example 11

(S)-3-(Naphth-2-yl)sulfonamido)-N-(1-carbamoyl-1-oxo-3-phenylpropan-2-yl)benzamide

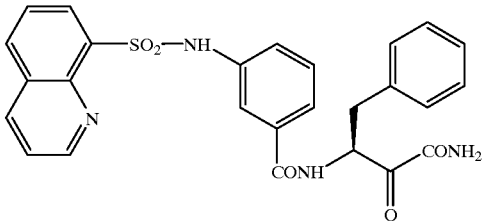

a) 8-Quinolyl-N-(3-ethoxycarbonyl)sulfonamide 5 g (30.3 mmol) of ethyl 3-aminobenzoate were reacted, at 0° C., with 8-quinolinesulfonyl chloride in analogy with Example 7a, with 5.9 g (76%) of product resulting.

b) N-(3-Carboxy)-8-quinolylsulfonamide 5.9 g of the intermediate compound 11a were hydrolyzed in analogy with Example 1b. Yield: 5.1 g (95%).

c) 3-(Naphth-2-yl)sulfonamido)-N-(3-(S)-1-carbamoyl-1-hydroxy-3-phenylpropan-2-yl)benzamide 1 g (3 mmol) of the intermediate compound 2b were reacted with 0.95 g (3 mmol) of the compound 11b in analogy with Example 2c, with 1.3 g (87%) of product resulting.

d) (S)-3-(2-Naphthyl)sulfonamido)-N-(1-carbamoyl-1-oxo-3-phenylpropan-2-yl)benzamide 1.2 g (2.4 mmol) of the intermediate compound 11c were oxidized in analogy with Example 1f. Yield: 0.8 g (70%).

1H NMR (D$_6$-DMSO): δ=2.9(1H), 3.1(1H), 5.2(1H), 7.0–8.8(17), 8.1(1H) and 10.2(1H) ppm.

Example 12

(S)-4-(2-Bromophenylsulfonamido)methyl-N-(1-carbamoyl-1-oxo-3-phenylpropan-2-yl)benzamide

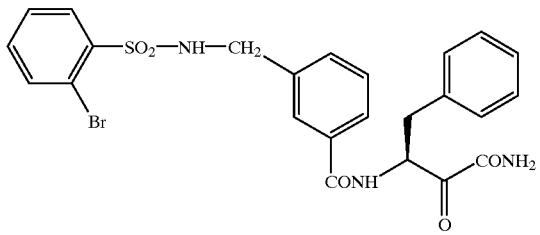

a) O-(tert-Butyl) N-(4-ethoxycarbonylbenzyl)carbamate 7 g (34.7 mmol) of ethyl 4-aminomethylbenzoate and 9.6 ml (39.4 mmol) of triethylamine were dissolved in 150 ml of tetrahydrofuran/dimethylformamide (2:1), and a solution of 8 g (36.5 mmol) of BOC anhydride in 100 ml of tetrahydrofuranwas added dropwise at 0° C. The whole was stirred at room temperature for 16 h. The mixture was then concentrated under reduced pressure and the residue was partitioned between water and ethyl acetate. The organic phase was dried and concentrated under reduced pressure, with 8.5 g (93%) of product resulting.

b) O-(tert-Butyl) N-(4-carboxybenzyl)carbamate 8.3 g (31.3 mmol) of the intermediate compound 12a were hydrolyzed in analogy with Example 8c, with 7.3 g (93%) of product resulting.

c) 4-(tert-Butyloxyamido)methyl-N-(-3-(S)-1-carbamoyl-1-hydroxy-3-phenylpropan-2-yl)benzamide 7 g (27.9 mmol) of the intermediate compound 12b were reacted with the compound 2b in analogy with Example 2c. Yield: 9.2 g (77%).

d) 4-Aminomethyl-N-(2-(S)-1-carbamoyl-1-hydroxy-3-phenylpropan-2-yl)benzamide 9.0 g (21 mmol) of the intermediate compound 12c were cleaved with trifluoroacetic acid in analogy with Example 1d. Yield: 10.8 g (100%).

e) 4-(Bromophenylsulfonamido)methyl-N-(2-(S)-1-carbamoyl-1-hydroxy-3-phenylpropan-2-yl)benzamide 1.5 g (3.4 mmol) of the intermediate compound 12d were reacted with 2-bromobenzenesulfonyl chloride at 0° C. in analogy with Example 7a, with 1.2 g (69%) of product resulting.

f) (S)-4-(2-Bromophenylsulfonamido)methyl-N-(1-carbamoyl-1-oxo-3-phenylpropan-2-yl)benzamide 1.05 g (1.9 mmol) of the intermediate compound 12e were oxidized in analogy with Example 1f. Yield: 0.78 g (75%).

1H NMR ($D_6$-DMSO): δ=2.9(1H), 3.2(1H), 4.2(2H), 5.3 (1H), 7.0–8.0(15H), 8.4(1H) and 8.8(1H) ppm.

Example 13

(S)-N-(1-N-(3-Morpholin-1-yl-3-propan-1-yl)carbamoyl-1-oxo-3-phenylpropan-2-yl)-2-(naphth-2-ylmethyl)benzamide

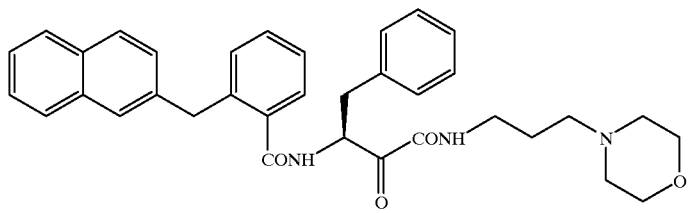

a) O-(tert-Butyl) N-(2-(S)-1-(N-3-morpholin-1-ylpropan-1-yl)carbamoyl-2-hydroxy-3-phenylpropan-2-yl)carbamate 19.2 g (65 mmol) of O-(tert-butyl) 2-(S)-N-(1-carboxy-2-hydroxy-3-phenylpropan-1-ol-2-yl)carbamate (S. L. Harbeson et al., J. Med. Chem. 1994, 37, 2918–29) were reacted with 1-(aminopropan-1-yl)morpholine in analogy with Example 2c, with 23.5 g (85%) of product resulting.

b) 3-(S)-3-Amino-2-hydroxy-N-(3-morpholin-1-ylpropan-1-yl)-4-phenylbutyramide 23.3 g (55.3 mmol) of the intermediate compound 13a were cleaved with trifluoroacetic acid in analogy with Example 1d, resulting in 28 g of crude product, which was subjected to further reaction without being purified.

c) N-(2-(S)-1-N-(3-Morpholin-1-ylpropan-1-yl)carbamoyl-1-hydroxy-3-phenylpropan-2-yl)-2-(naphth-2-ylmethyl)benzamide 1.57 g (6 mmol) of the intermediate compound 6c were reacted with the compound 13b in analogy with Example 2c. Yield: 1.1 g (32%).

d) (S)-N-(1-N-(3-Morpholin-1-yl-3-propan-1-yl)carbamoyl-1-oxo-3-phenylpropan-2-yl)-2-(naphth-2-ylmethyl)benzamide 0.57 g (1 mmol) of the intermediate compound 13c was oxidized in analogy with Example 2c. Yield: 0.14 g (25%).

1H NMR ($D_6$-DMSO): δ=1.6(2H), 2.2(6H), 2.9(1H), 3.2 (3H), 3.5(4H), 4.1(2H), 5.3(1H), 7.0–7.9(16H) and 8.9(1H) ppm.

Example 14

(S)-N-(1-N-(3-Morpholin-1-yl-3-propan-1-yl) carbamoyl-1-oxo-3-phenylpropan-2-yl)-4-(napth-2-ylamido)methylbenzamide

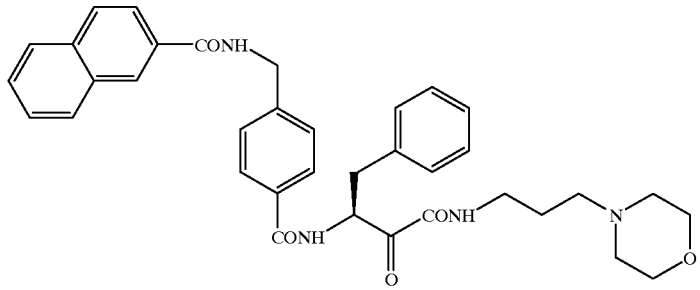

a) N-(2-(S)-1-N-(3-Morpholin-1-yl-3-propan-1-yl)carbamoyl-1-hydroxy-3-phenylpropan-2-yl)-4-(napth-2-ylamidomethyl)-benzamide 3.1 g (10 mmol) of the intermediate compound 4a were reacted with the compound 13b in analogy with Example 2c, with 1.9 g of product being obtained.

b) (S)-(1-N-(3-Morpholin-1-yl-3-propan-1-yl)carbamoyl-1-oxo-3-phenylpropan-2-yl)-4-(napth-2-ylamido)methylbenzamide 1.2 g (2 mmol) of the intermediate compound 14a were oxidized in analogy with Example 1f. Yield: 0.83 g (73%).

1H NMR (D$_6$-DMSO): δ=1.6(2H), 2.2(6H), 3.0(1H), 3–3.2(3H), 3.5(4H), 4.6(2H), 5.2(1H), 6.9–8.0(16H), 8.4(1H), 8.8(1H) and 9.0(1H) ppm.

Example 15

(S)-N-(1-N-(3-Morpholin-1-ylpropan-1-yl) carbamoyl-1-oxo-3-phenylpropan-2-yl)-2-phenylbenzamide

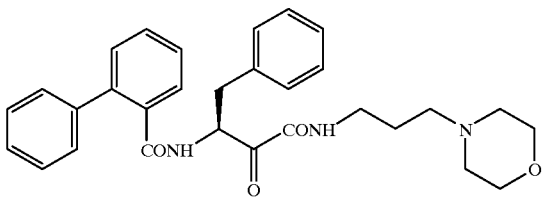

a) N-(2-(S)-1-N-(3-Morpholin-1-yl propan-1-yl)carbamoyl-1-hydroxy-3-phenylpropan-2-yl)-2-phenylbenzamide 2 g (10 mmol) of 2-biphenylcarboxylic acid were reacted with the intermediate compound 13b in analogy with Example 2c, with 1.8 g of product being obtained.

b) (S)-N-(1-N-(3-Morpholin-1-ylpropan-1-yl)carbamoyl-1-oxo-3-phenylpropan-2-yl)-2-phenylbenzamide 1.0 g (2 mmol) of the intermediate compound 15a was oxidized in analogy with Example 1f. Yield: 0.45 g (45%).

1H NMR (D$_6$-DMSO): δ=1.7(2H), 2.2(6H), 2.8(1H), 3.2(3H), 3.6(4H), 5.2(1H), 7.0–7.8(14H) and 8.9(2H) ppm.

Example 16

(S)-2-Methyl-N-(1-N-(3-morpholin-1-ylpropan-1-yl) carbamoyl-1-oxo-3-phenylpropan-2-yl)-5-(naphth-2-yl-sulfonamido)benzamide

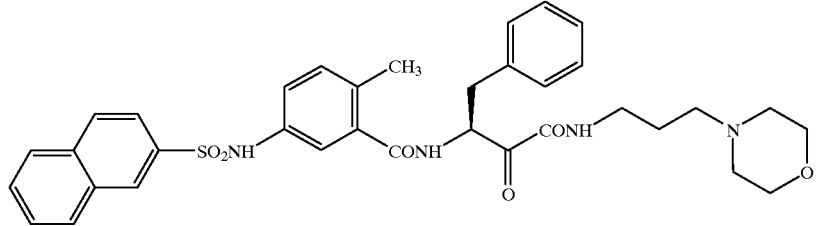

a) Ethyl 5-amino-2-methylbenzoate 26.5 g (127 mmol) of ethyl 2-methyl-5-nitrobenzoate were hydrogenated in ethanol after having added 1 g of palladium/charcoal (10% strength). After filtering, the filtrate was concentrated under reduced pressure. Yield: 0.1 g (89%).

b) Ethyl 2-methyl-5-(naphth-2-ylsulfonamido)benzoate 12.6 g (70.4 mmol) of the intermediate compound 16a were reacted with 2-naphthalenesulfonyl chloride at 0° C. in analogy with Example 7a, with 20.1 g of product resulting.

c) 2-Methyl-5-(naphth-2-ylsulfonamido)benzoic acid 20 g (54 mmol) of the intermediate compound 16b were hydrolyzed in analogy with Example 8c, with 15.8 g of product being obtained.

d) 2-Methyl-N-(2-(S)-1-N-(3-morpholin-1-ylpropan-1-yl) carbamoyl-1-hydroxy-3-phenylpropan-2-yl)-5-(naphth-2-ylsulfonamido)benzamide 3.4 g (10 mmol) of the intermediate compound 16c were reacted with the compound 13b in analogy with Example 2c. Yield: 3.8 g.

e) (S)-2-Methyl-N-(1-N-(3-morpholin-1-ylpropan-1-yl) carbamoyl-1-oxo-3-phenylpropan-2-yl)-5-(naphth-2-ylsulfonamido)benzamide 0.92 g (1.5 mmol) of the intermediate compound was oxidized in analogy with Example 1f. Yield: 0.3 g (32%).

1H NMR (D$_6$-DMSO): δ=1.6(2H), 2.0(3H), 2.3(3H), 2.8 (1H), 3.2(2H), 3.2–3.5(3H), 3.6(4H), 5.2(1H), 6.9–8.1 (14H), 8.3(1H), 8.7(1H), 8.9(1H) and 10.4(1H) ppm.

Example 17

(S)-N-(1-Carbamoyl-1-oxo-3-phenylpropan-2-yl)-2-methyl-5-(naphth-2-ylsulfonamido)benzamide

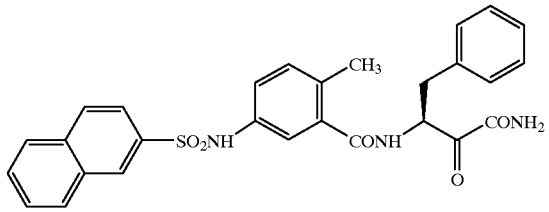

a) N-(2-(S)-1-Carbamoyl-1-hydroxy-3-phenylpropan-2-yl)-2-methyl-5-(naphth-2-ylsulfonamido)benzamide 2.7 g (8 mmol) of the intermediate compound 16c were reacted with the compound 2b in analogy with Example 2c. Yield: 1.5 g (46%).

b) (S)-N-(1-Carbamoyl-1-oxo-3-phenylpropan-2-yl)-2-methyl-5-(naphth-2-ylsulfonamido)benzamide 1.0 g (2 mmol) of the intermediate compound 17a was oxidized in analogy with Example 1f. Yield: 0.65 g (65%).

1H NMR (D$_6$-DMSO): δ=2.0(3H), 2.8(1H), 3.2(1H), 5.2 (1H), 6.8–8.0(15H), 8.2(2H), 8.6(1H) and 10.2(1H) ppm.

Example 18

(S)-N-(1-Carbamoyl-1-oxo-3-phenylpropan-2-yl)-4-(quinoxalin-2-ylamido)methylbenzamide

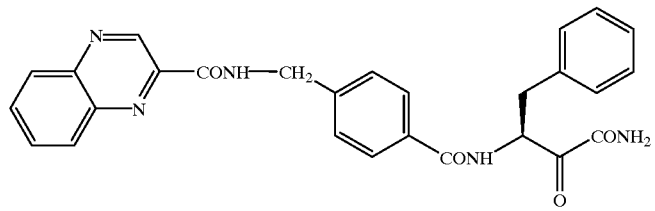

a) N-(2-(S)-1-Carbamoyl-1-hydroxy-3-phenylpropan-2-yl)-4-(quinoxalin-2-ylamido)methylbenzamide 1.2 g (2.7 mmol) of the intermediate compound 12d were reacted with 2-quinoxalinecarbonyl chloride in analogy with Example 7a, with 0.8 g (62%) of product resulting.

b) (S)-N-(1-Carbamoyl-1-oxo-3-phenylpropan-2-yl)-4-(quinoxalin-2-ylamido)methylbenzamide 0.78 g (1.6 mmol) of the intermediate compound 18a was oxidized in analogy with Example 1f. Yield: 0.42 g (55%). MS: m/e=481 (M$^+$).

Example 19

(S)-N-(1-Carbamoyl-1-oxo-3-phenylpropan-2-yl)-4-(quinolin-4-ylamido)methylbenzamide

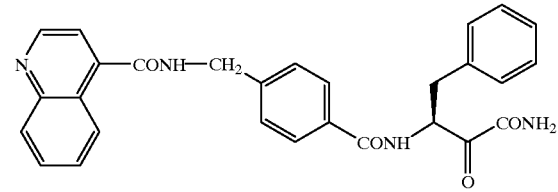

a) N-(2-(S)-1-Carbamoyl-1-hydroxy-3-phenylpropan-2-yl)-4-(quinolin-4-ylamido)methylbenzamide 0.8 g (1.8 mmol) of the intermediate compound 12d was reacted with 4-quinolinecarboxylic acid in analogy with Example 2c, with 0.4 g (46%) of product resulting.

b) (S)-N-(1-Carbamoyl-1-oxo-3-phenylpropan-2-yl)-4-(quinolin-4-ylamido)methylbenzamide 0.39 g (0.8 mmol) of the intermediate compound 19a was oxidized in analogy with Example 1f. Yield: 0.27 g (70%).

1H NMR (D$_6$-DMSO): δ=2.9(1H), 3.1(1H), 4.4(2H), 5.2 (1H), 7.0–8.0(15H), 8.8(1H), 8.9(1H) and 9.3(2H) ppm.

Example 20

(S)-N-(1-Carbamoyl-1-oxo-3-phenylpropan-2-yl)-4-(quinoxalin-6-ylamido)methylbenzamide

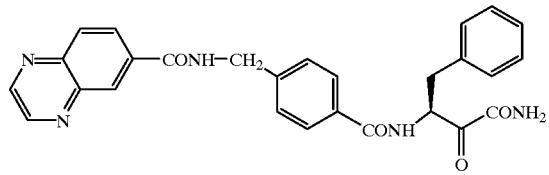

a) N-(2-(S)-1-Carbamoyl-1-hydroxy-3-phenylpropan-2-yl)-4-(quinoxalin-6-ylamido)methylbenzamide 0.8 g (1.8 mmol) of the intermediate compound 12d was reacted with 6-quinoxalinecarboxylic acid in analogy with Example 2c, with 0.36 g (42%) of product resulting.

b) (S)-N-(1-Carbamoyl-1-oxo-3-phenylpropan-2-yl)-4-(quinoxalin-6-ylamido)methylbenzamide 0.35 g (0.72 mmol) of the intermediate compound 20a was oxidized in analogy with Example 1f. Yield: 0.23 g (66%).

1H NMR (D$_6$-DMSO): δ=2.8(1H), 3.2(1H), 4.6(2H), 5.2 (1H), 7.0–8.2(10H), 8.7(1H), 8.8(1H), 9.0(2H) and 9.4(2H) ppm.

Example 21

(S)-N-(1-Carbamoyl-1-oxo-3-phenylpropan-2-yl)-4-(quinolin-6-ylamido)methylbenzamide

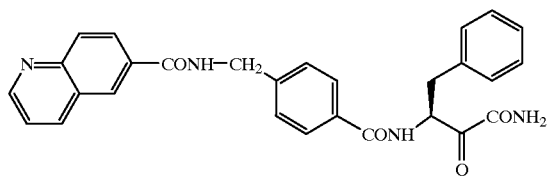

a) N-(2-(S)-1-Carbamoyl-1-hydroxy-3-phenylpropan-2-yl)-4-(quinolin-6-ylamido)methylbenzamide 0.8 g (1.8 mmol) of the intermediate compound 12d were reacted with 6-quinolinecarboxylic acid in analogy with Example 2c, with 0.41 g (47%) of product resulting.

b) (S)-N-(1-Carbamoyl-1-oxo-3-phenylpropan-2-yl)-4-(quinolin-6-ylamido)methylbenzamide 0.4 g (0.83 mmol) of the intermediate compound 21a was oxidized in analogy with Example 1f. Yield: 0.34 g (85%).

1H NMR (D$_6$-DMSO): δ=2.9(1H), 3.1(1H), 4.4(2H), 5.2 (1H) and 7.0–9.2(19H) ppm.

Example 22

(S)-N-(1-Carbamoyl-1-oxo-3-phenylpropan-2-yl)-4-(quinolin-3-ylamido)methylbenzamide

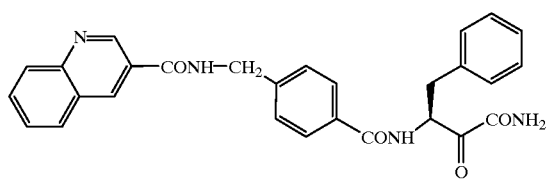

a) N-(2-(S)-1-Carbamoyl-1-hydroxy-3-phenylpropan-2-yl)-4-(quinoxalin-3-ylamido)methylbenzamide 1.0 g (2.3 mmol) of the intermediate compound 12d were reacted with 3-quinoxalinecarboxylic acid in analogy with Example 2c, with 0.89 g (80%) of product resulting.

b) (S)-N-(1-Carbamoyl-1-oxo-3-phenylpropan-2-yl)-4-(quinoxalin-6-ylamido)methylbenzamide 0.84 g (1.7 mmol) of the intermediate compound 22a was oxidized in analogy with Example 1f. Yield: 0.75 g (90%). MS: m/e=480 (M$^+$).

Example 23

N-(1-Ethoxycarbonyl-1-oxo-3-phenylpropan-2-yl)-4-(naphth-2-ylamido)benzamide

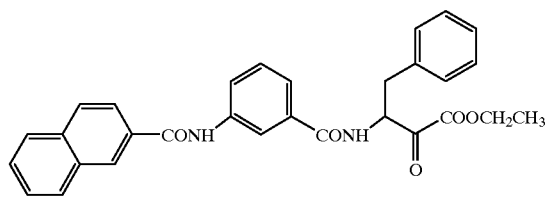

a) 3-(Naphth-2-ylamido)benzoic acid 14.8 g (0.11 mol) of 3-aminobenzoic acid were dissolved in 300 ml of pyridine, and 20.6 g (0.11 mol) of 2-naphthoyl chloride were added in portions. The whole was stirred at room temperature for 16 h. The mixture was then concentrated under reduced pressure and the residue was recrystallized from ethanol. Yield: 30.3 g (97%).

b) N-(1-Ethoxycarbonyl-3-phenylpropan-2-yl)-4-(naphth-2-ylamido) benzamide 18.0 g (61.8 mmol) of the intermediate compound 23a and 14.2 g (61.8 mmol) of D,L-alanine ethyl ester were reacted in analogy with Example 2c, with 19.8 g (71%) of product being obtained.

c) N-(1-Carboxy-3-phenylpropan-2-yl)-4-(naphth-2-ylamido)benzamide 19.5 g (41.8 mmol) of the intermediate compound 23b were hydrolyzed in analogy with Example 8c. Yield: 15.2 g (83%).

d) N-(1-Ethoxycarbonyl-1-oxo-3-phenylpropan-2-yl)-4-(naphth-2-ylamido)benzamide 7.1 ml (63.9 mmol) of ethyl oxalyl chloride were added dropwise to a solution of 14.0 g (32 mmol) of the intermediate compound 23c, 0.4 g (3.2 mmol) of N,N-4-dimethylaminopyridine and 10.3 ml (127.7 mmol) of pyridine in 100 ml of anhydrous tetrahydrofuran such that the temperature rose to approx. 40° C. The whole was then boiled under reflux for 3 h. It was then stirred at room temperature for a further 16 h. 100 ml of water were then added carefully and the mixture was stirred once again for 30 min. A large quantity of water was added to the reaction mixture and the whole was extracted with ethyl acetate. The organic phase was dried and concentrated under reduced pressure, thereby yielding 17 g of an oil. This oil was dissolved in 100 ml of absolute ethanol and 0.24 g of potassium tert-butoxide was added. The mixture was stirred at room temperature for a further 16 h. It was then concentrated under reduced pressure and the residue was purified by is chromatography (mobile solvent: methylene chloride/ethyl acetate=10/1). Yield: 7.5 g (54%).

1H NMR (CDCl$_3$): δ=1.3(3H), 3.2(1H), 3.3(1H), 4.2(2H), 5.6(1H) and 6.9–8.4(18H) ppm.

Example 24

(S)-N-(1-Ethoxycarbonyl-1-oxo-3-phenylpropan-2-yl)-2-phenylbenzamide

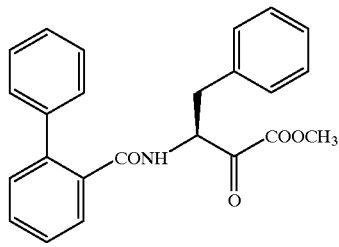

a) N-(3-(S)-1-Ethoxycarbonyl-1-hydroxy-3-phenylpropan-2-yl)-2-phenylbenzamide

2-Biphenylcarboxylic acid was reacted with methyl 3-(S)-3-amino-2-hydroxy-4-phenylbutyrate in analogy with Example 2c.

b) (S)-N-(1-Ethoxycarbonyl-1-oxo-3-phenylpropan-2-yl)-2-phenylbenzamide

The intermediate compound 24a was oxidized in analogy with Example 1f. MS: m/e=387 (M$^+$).

Example 25

(S)-N(N-Carboxymethyl-1-carbamoyl-1-oxo-3-phenylpropan-2-yl)-3-(2-naphthylsulfonamido)benzamide

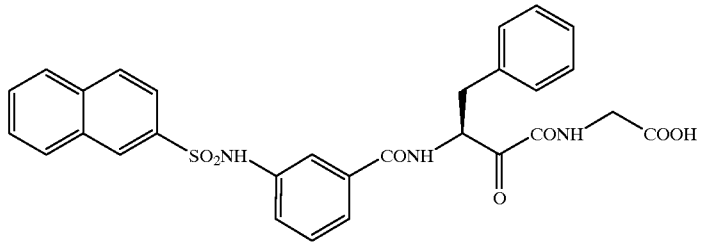

a) O-tert-Butyl-N(3(S)-1-ethoxycarbonyl-2-hydroxy-4-phenylpropan-2-yl)urethane 2.3 g (7.7 mMol [sic]) of O-tert-butyl-N-(3(S)-1-carboxy-2-hydroxy-4-phenylpropan-2-yl)urethane and 1.1 g (7.7 mmol) of glycine ethyl ester hydrochloride were reacted in analogy with Example 2c, with 1.7 g (57%) of the product being obtained.

b) 3(S)-3-Amino-N-(ethoxycarbonylmethyl)-2-hydroxy-4-phenyl-butyramide×trifluoroacetic acid 1.4 g (3.7 mMol [sic]) of the intermediate compound 25a were dissolved in 25 ml of methylene chloride and this solution was stirred at room temperature for 2 h after 10 ml of trifluoroacetic acid had been added. The whole was then concentrated under reduced pressure, with 1.5 g (100%) of the product resulting.

c) (S)-N(1-(N-Ethoxycarbonylmethylcarbamoyl)-1-hydroxy-3-phenylpropan-2-yl)-3-(2-naphthylsulfonamido)benzamide The intermediate compound 7b was reacted with the product 25b in analogy with Example 2c. Yield: 1.3 g d) (S)-N(1-(N-Carboxymethylcarbamoyl)-1-hydroxy-3-phenylpropan-2-yl)-3-(2-naphthylsulfonamido)benzamide 1.2 g (2 mMol [sic]) of the intermediate compound 25c were hydrolyzed with lithium hydroxide in analogy with Example 8c. Yield: 0.77 g (67%).

e) (S)-N(1-(N-Carboxymethylcarbamoyl)-1-oxo-3-phenylpropan-2-yl)-3-(2-naphthylsulfonamido)benzamide 0.7 g (1.2 mMol [sic]) of the intermediate compound 25d were oxidized in analogy with Example 1f, with 0.16 g (23%) of the product being obtained. MS: m/e=559 (M$^+$).

Example 26

N-(1-Carbamoyl-1-oxo-3-phenylpropan-2-yl)-3-(2-naphthylsulfonamido)benzamide

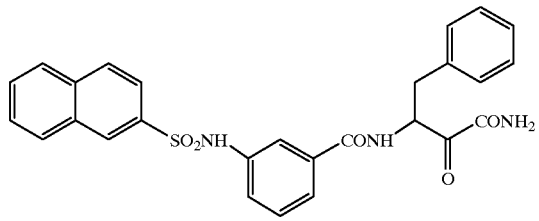

a) The intermediate compound 7b was reacted with ethyl 3-amino-2-hydroxy-4-phenylbutyrate in analogy with Example 2c.

b) N(N-Carboxymethyl-1-carbamoyl-1-oxo-3-phenylpropan-2-yl)-3-(2-naphthylsulfonamido)benzamide The intermediate compound 26a was oxidized in analogy with Example 1f, with the product being obtained.

$^1$H-NMR (D$_6$-DMSO): δ=2.5(2H), 5.2(1H), 7.1–8.1 (17H), 8.4(2H), 8.8(1H) and 10.5(1H) ppm.

The following can be prepared in an analogous manner:

| Example | Stereo-chemistry at C-2 | R¹ | X | R² | R³ | R⁴ |
|---|---|---|---|---|---|---|
| 27 | (S) | 2-methylnaphthyl | 4-CH=CH-C(O)- | H | CH₂—Ph | NH₂ |
| 28 | (S) | 1-methylnaphthyl | 4-CH=CH-C(O)- | H | CH₂—Ph | NH₂ |
| 29 | (S) | 2-methylnaphthyl | 4-CH=CH-C(O)- | H | CH₂—Ph | —NHCH₂CH₂CH₂-morpholine |
| 30 | (S) | 2-methylnaphthyl | 4-CH=CH-C(O)- | H | CH₂—Ph | —(CH₂)₃-piperidine |
| 31 | (R,S) | naphthyl | 4-CH=CH-C(O)- | H | —(CH₂)₃CH₃ | NH₂ |
| 32 | (S) | 4-methylpyridyl | 2-CH=CH- | H | CH₂—Ph | NH₂ |

-continued

| Example | Stereo-chemistry at C-2 | R¹ | X | R² | R³ | R⁴ |
|---|---|---|---|---|---|---|
| 33 | (S) | 4-pyridyl | 2-CH=CH- | H | CH₂—Ph | NHCH₂CH₃ |
| 34 | (R,S) | 4-pyridyl | 2-CH=CH- | H | CH₂CH₂CH₂CH₃ | NH₂ |
| 35 | (S) | 4-pyridyl | 2-CH=CH- | H | CH₂Ph | 4-methylpiperazinyl-ethylamino |
| 36 | (S) | 2-pyridyl | 2-CH=CH-CH₂- | H | CH₂—Ph | NH₂ |
| 37 | (S) | 2-pyridyl | 2-CH=CH-CH₂- | H | CH₂—Ph | morpholinyl-ethylamino |
| 38 | (S) | 2-pyridyl | 2-CH=CH-CH₂- | H | CH₂—Ph | NHCH₂CH₃ |
| 39 | (R,S) | 2-methylnaphthyl | 4-SO₂NHCH₂- | H | CH₂—Ph | NH₂ |

-continued

| Example | Stereo-chemistry at C-2 | R¹ | X | R² | R³ | R⁴ |
|---|---|---|---|---|---|---|
| 40 | (R,S) | 2-methylnaphthyl | 4-SO$_2$NHCH$_2$ | H | CH$_2$—Ph | NHCH$_2$CH$_2$CH$_3$ |
| 41 | (S) | thienyl | 4-CONH— | H | CH$_2$—Ph | NH$_2$ |
| 42 | (S) | 2-methylnaphthyl | 3-SO$_2$NH | 6-CH$_3$ | CH$_2$—Ph | NH$_2$ |
| 43 | (S) | 2-methylnaphthyl | 3-SO$_2$NH | 6-CH$_3$ | CH$_2$-cyclohexyl | NH$_2$ |
| 44 | (R,S) | 2-methylnaphthyl | 3-SO$_2$NH | 6-CH$_3$ | CH$_2$CH$_2$CH$_3$ | NH$_2$ |
| 45 | (S) | 2-methylnaphthyl | 3-SO$_2$NH | 6-CH$_3$ | CH$_2$—Ph | morpholino-propyl-NH |
| 46 | (S) | 2-methylnaphthyl | 3-SO$_2$NH | 6-CH$_3$ | CH$_2$—Ph | pyrrolidino-ethyl-NH |

-continued

| Example | Stereo-chemistry at C-2 | R¹ | X | R² | R³ | R⁴ |
|---|---|---|---|---|---|---|
| 47 | (S) | Ph— | 3-SO$_2$NH | H | CH$_2$—Ph | NH$_2$ |
| 48 | (R,S) | Ph | 3-SO$_2$NH | 6-CH$_3$ | CH$_2$—Ph | NH$_2$ |
| 49 | (S) | Ph | 3-SO$_2$NH | H | CH$_2$—Ph | morpholinopropyl-NH |
| 50 | (S) | Ph | 3-SO$_2$NH | H | CH$_2$—Ph | NHCH$_2$CH$_3$ |
| 51 | (S) | Ph | 3-SO$_2$NH | H | CH$_2$—Ph | N-methylpiperazinyl-propyl-NH |
| 52 | (R,S) | Ph | 3-SO$_2$NH | 6-CH$_3$ | CH$_2$CH$_2$CH$_2$CH$_3$ | NH$_2$ |
| 53 | (S) | Ph | 3-SO$_2$NH | 6-CH$_3$ | CH$_2$CH$_2$CH$_2$CH$_3$ | NH$_2$ |
| 54 | (R,S) | 4-pyridyl | 2-CH=CH | H | CH$_2$CH$_2$CH$_3$ | NH$_2$ |
| 55 | (R,S) | 4-pyridyl | 2-CH=CH | H | CH$_2$CH$_2$CH$_3$ | morpholinopropyl-NH |
| 56 | (R,S) | 4-pyridyl | 2-CH=CH | H | CH$_2$CH$_2$CH$_3$ | NHCH$_2$CH$_3$ |
| 57 | (S) | 3-methylnaphthyl | 3-C(O)CH=CH | H | CH$_2$—Ph | NH$_2$ |

-continued

| Example | Stereo-chemistry at C-2 | R¹ | X | R² | R³ | R⁴ |
|---|---|---|---|---|---|---|
| 58 | (S) | naphthyl | 3-C(O)CH=CHCH₃ | H | CH₂—Ph | piperidinyl-ethyl-NH |
| 59 | (S) | naphthyl | 2-CH₂—O— | H | CH₂—Ph | NH₂ |
| 60 | (S) | naphthyl | 2-CH₂ | H | CH₂—Ph | NH₂ |
| 61 | (R,S) | naphthyl | 2-CH₂ | H | CH₂CH₂CH₂CH₃ | NH₂ |
| 62 | (R,S) | naphthyl | 2-CH₂ | H | CH₂Ph | N(Et)₂-propyl-NH |
| 63 | (R,S) | 3,4-dimethoxyphenyl | 4-C(O)CH=CHCH₃ | H | CH₂Ph | NH₂ |
| 64 | (R,S) | benzothienyl | 3-C(O)CH=CHCH₃ | H | CH₂Ph | NH₂ |

-continued
| Example | Stereo-chemistry at C-2 | R¹ | X | R² | R³ | R⁴ |
|---|---|---|---|---|---|---|
| 65 | (R,S) | 4-pyridyl | 3-(CO-CH=CH-CH₃) | H | CH₂Ph | NH₂ |
| 66 | (R,S) | 4-pyridyl | 1,4-phenylene | H | CH₂Ph | NH₂ |
| 67 | (R,S) | 4-pyridyl | 1,4-phenylene | H | CH₂Ph | morpholinopropyl-NH |
| 68 | (R,S) | 2-pyridyl | 1,4-phenylene | H | CH₂Ph | NH₂ |
| 69 | (R,S) | 3,4-dimethoxy-6-methylphenyl | 2≡ | H | CH₂Ph | NH₂ |
| 70 | (R,S) | 3,4-dimethoxy-6-methylphenyl | 2≡ | H | CH₂Ph | piperidinoethyl-NH |
| 71 | (R,S) | 7-methyl-2-naphthyl | 3-SO₂NH | H | CH₂Ph | piperidinopropyl-NH |

-continued
| Example | Stereo-chemistry at C-2 | $R^1$ | X | $R^2$ | $R^3$ | $R^4$ |
|---|---|---|---|---|---|---|
| 72 | (R,S) | 2-naphthyl | 3-SO$_2$NH | H | CH$_2$Ph | 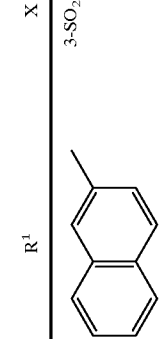 |
| 73 | (R,S) | 2-naphthyl | 3-SO$_2$NH | H | CH$_2$Ph | 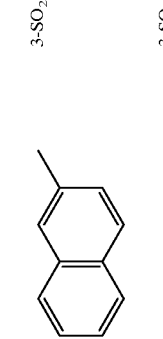 |
| 74 | (R,S) | 2-naphthyl | 3-SO$_2$NH | H | CH$_2$Ph | 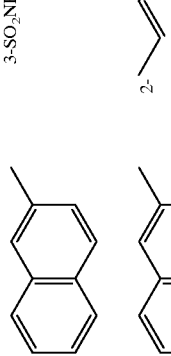 |
| 75 | (R,S) | 2-naphthyl | 2-CH=CH | 5-NO$_2$ | CH$_2$Ph | NH$_2$ |
| 76 | (R,S) | 2-naphthyl | 2-CH=CH | 5-NO$_2$ | CH$_2$Ph | NHCH$_2$CH$_2$CH$_3$ |
| 77 | (R,S) | 2-naphthyl | 2-CH=CH | 5-NHCOCH$_3$ | CH$_2$Ph | NH$_2$ |
| 78 | (R,S) | 2-naphthyl | 2-CH=CH | 5-NHCOPh | CH$_2$Ph | NH$_2$ |

-continued

General structure:
R¹—X—[benzene ring with (R²)ₙ, positions 1-6]—C(=O)—NH—CH(R³)—C(=O)—C(=O)—R⁴ (C-2 is the CH)

| Example | Stereo-chemistry at C-2 | R¹ | X | R² | R³ | R⁴ |
|---|---|---|---|---|---|---|
| 79 | (R,S) | 2-naphthyl | 5-SO$_2$NH— | 2-CH=CH-Ph | CH$_2$Ph | NH$_2$ |
| 80 | (R,S) | 2-naphthyl | 5-SO$_2$NH— | 2-CH=CH-Ph | CH$_2$Ph | NH-CH$_2$CH$_2$CH$_2$-N(4-methylpiperazinyl) |
| 81 | (R,S) | 2-naphthyl | 4-SCH$_2$— | H | CH$_2$Ph | NH$_2$ |
| 82 | (R,S) | 2-naphthyl | 4-SCH$_2$— | H | CH$_2$Ph | NH-CH$_2$CH$_2$-N(piperidinyl) |
| 83 | (R,S) | 2-naphthyl | 4-SCH$_2$— | H | CH$_2$Ph | NH-CH$_2$CH$_2$CH$_3$ |
| 84 | (R,S) | 2-naphthyl | 4-SO$_2$— | H | CH$_2$Ph | NH-CH$_2$CH$_2$CH$_2$-N(4-methylpiperazinyl) |
| 85 | (R,S) | 4-pyridyl | 2-CH=CH-CH$_2$— | H | CH$_2$Ph | NH-CH$_2$CH$_2$CH$_2$-N(4-methylpiperazinyl) |

-continued

| Example | Stereo-chemistry at C-2 | R¹ | X | R² | R³ | R⁴ |
|---|---|---|---|---|---|---|
| 86 | (R,S) | 4-pyridyl | 2-CH=CH- | H | CH₂Ph | 2-pyridylethyl-NH |
| 87 | (R,S) | 4-pyridyl | 2-CH=CH- | H | CH₂Ph | 1-methylpiperidin-4-yl-NH |
| 88 | (R,S) | 4-pyridyl | 2-CH=CH- | H | CH₂Ph | 1-benzylpiperidin-4-yl-NH |
| 89 | (R,S) | 4-pyridyl | 2-CH=CH- | H | CH₂Ph | 4-methylpiperazin-1-yl-ethyl-NH |
| 90 | (R,S) | 4-pyridyl | 2-CH=CH- | H | CH₂Ph | piperidin-1-yl-propyl-NH |
| 91 | (R,S) | 4-pyridyl | 2-CH=CH- | H | CH₂Ph | pyrrolidin-1-yl-propyl-NH |
| 92 | (R,S) | 4-pyridyl | 2-CH=CH- | H |  | imidazol-1-yl-propyl-NH |

-continued

| Example | Stereo-chemistry at C-2 | R¹ | X | R² | R³ | R⁴ |
|---|---|---|---|---|---|---|
| 93 | (R,S) | 4-methylpyridine | 2-, trans-CH=CH | H | $CH_2CH_2CH_2CH_3$ | $NH_2$ |
| 94 | (R,S) | 3-methylpyridine | 2-, trans-CH=CH | H | $CH_2CH_2CH_2CH_3$ | 3-(4-methylpiperazin-1-yl)propylamino |
| 95 | (R,S) | 3-methylpyridine | 2-, trans-CH=CH | H | $CH_2Ph$ | $NH_2$ |
| 96 | (R,S) | 3-methylpyridine | 2-, trans-CH=CH | H | $CH_2Ph$ | 4-(morpholin-4-yl)butylamino |
| 97 | (R,S) | 3-methylpyridine | 2-, trans-CH=CH | H | $CH_2Ph$ | 3-(4-methylpiperazin-1-yl)propylamino |
| 98 | (R,S) | 3-methylpyridine | 2-, trans-CH=CH | H | $CH_2Ph$ | 2-(piperidin-1-yl)ethylamino |
| 99 | (R,S) | 3-methylpyridine | 2-, trans-CH=CH | H | $CH_2Ph$ | 3-(pyridin-2-yl)propylamino |

-continued

| Example | Stereo-chemistry at C-2 | R¹ | X | R² | R³ | R⁴ |
|---|---|---|---|---|---|---|
| 100 | (R,S) | 3-methylpyridine | 2-, trans-CH=CH | H | CH₂Ph | NH-(CH₂)₃-CH₃ |
| 101 | (R,S) | 3-methylquinoline | 2-, trans-CH=CH | H | CH₂Ph | NH₂ |
| 102 | (R,S) | 3-methylquinoline | 2-, trans-CH=CH | H | CH₂Ph | NH-(CH₂)₃-CH₃ |
| 103 | (R,S) | 3-methylquinoline | 2-, trans-CH=CH | H | CH₂Ph | NH-CH₂-CH₂-(3-pyridyl) |
| 104 | (R,S) | 3-methylquinoline | 2-, trans-CH=CH | H | CH₂Ph | NH-(CH₂)₃-morpholinyl |
| 105 | (R,S) | 3-methylquinoline | 2-, trans-CH=CH | H | CH₂Ph | NH-(CH₂)₃-(4-N-methylpiperazinyl) |
| 106 | (R,S) | 3-methylquinoline | 2-, trans-CH=CH | H | CH₂Ph | NH₂ |

-continued

| Example | Stereo-chemistry at C-2 | R¹ | X | R² | R³ | R⁴ |
|---|---|---|---|---|---|---|
| 107 | (R,S) | 3-quinolinyl | 2-CH=CH- | H | CH₂Ph | morpholinopropyl-NH- |
| 108 | (R,S) | 3-quinolinyl | 2-CH=CH- | H | CH₂Ph | piperidinopropyl-NH- |
| 109 | (R,S) | 3-benzothienyl | 2-CH=CH- | H | CH₂Ph | NH₂ |
| 110 | (R,S) | 3-benzothienyl | 2-CH=CH- | H | CH₂Ph | (4-methylpiperazinyl)propyl-NH- |
| 111 | (R,S) | 3-benzothienyl | 2-CH=CH- | H | CH₂Ph | morpholinopropyl-NH- |
| 112 | (R,S) | 2-benzothienyl | 2-CH=CH- | H | CH₂Ph | 4-phenylbutyl-NH- |

We claim:
1. A ketobenzamide of the formula I

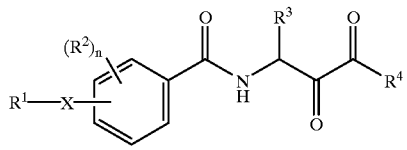

and its tautomeric and isomeric forms, and also, where appropriate, its physiologically tolerated salts, where the variables have the following meanings:

$R^1$ is phenyl, naphthyl, quinolyl, pyridyl, pyrimidyl, pyrazyl, pyridazyl, quinazolyl, quinoxalyl, thienyl, benzothienyl, benzofuryl, benzimidazolyl, furanyl, indolyl, isoquinoline, tetrahydroisoquinoline or tetrahydroquinoline, where the aromatic and heteroaromatic rings can additionally be substituted by one, two or three $R^5$ radicals, $R^2$ is chlorine, bromine, fluorine, $C_1$–$C_6$-alkyl, $C_2$–$C_6$-alkenyl, $C_2$–$C_6$-alkynyl, $C_1$–$C_6$-alkyl-phenyl, $C_2$–$C_6$-alkenyl-phenyl, $C_2$–$C_6$-alkynyl-phenyl, phenyl, NHCO—$C_1$–$C_4$-alkyl, —NHCO-phenyl, —NHCO-naphthyl, $H_2N$—$SO_2$—$C_{1-4}$-alkyl—, COOH, —COO—$C_{1-4}$-alkyl, —CONH—$C_{1-4}$-alkyl, $C_{1-4}$-alkoxy, $NO_2$ or $NH_2$, $R^3$ is $C_1$–$C_6$-alkyl which can also carry a phenyl, cyclopropyl, cyclobutyl, cyclopentyl, cyclohexyl, cycloheptyl, indolyl, pyridyl or naphthyl ring which, for its part, can be substituted by one or two $R^5$ radicals, X is a bond, —$(CH_2)_m$—, —$(CH_2)_m$—O—$(CH_2)_o$—, —$(CH_2)_n$—S—$(CH_2)_m$—, —$(CH_2)_n$—SO—$(CH_2)_m$—, —$(CH_2)_m$—, —$(CH_2)_n$—SO$_2$—$(CH_2)_m$—, —CH=CH—, —C≡C—, —CO—CH=CH—, CO—$(CH_2)_m$—, —$(CH_2)_m$—NHCO—$(CH_2)_o$—, —$(CH_2)_m$—CONH—$(CH_2)_o$—, —$(CH_2)_m$—NHSO$_2$—$(CH_2)_o$—, —NH—CO—CH=CH—, —CH=CH—CO—NH—, —$(CH_2)_m$—SO$_2$NH—$(CH_2)_o$— or

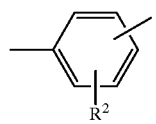

$R^4$ is $OR^6$, $NR^7R^8$,

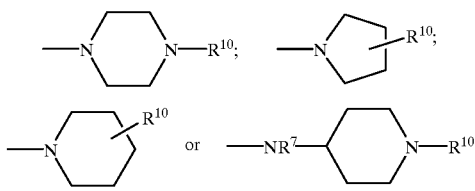

$R^5$ is hydrogen, $C_1$–$C_4$-alkyl, —O—$C_1$–$C_4$-alkyl, OH, Cl, F, Br, I, $CF_3$, $NO_2$, $NH_2$, CN, COOH, COO—$C_1$–$C_4$-alkyl, —NHCO—$C_1$–$C_4$-alkyl, —NHCO-phenyl, —NHSO$_2$—$C_1$–$C_4$-alkyl, —NHSO$_2$-phenyl, —SO$_2$—$C_1$–$C_4$-alkyl or —SO$_2$-phenyl, $R^6$ is hydrogen or $C_1$–$C_6$-alkyl which can be substituted by a phenyl ring which, itself, can also be substituted by one or two $R^9$ radicals, $R^7$ is hydrogen or $C_1$–$C_6$-alkyl, $R^8$ is hydrogen or $C_1$–$C_6$-alkyl which can also be substituted by a phenyl ring, which can carry one or two $R^9$ radicals, or by one of the radicals

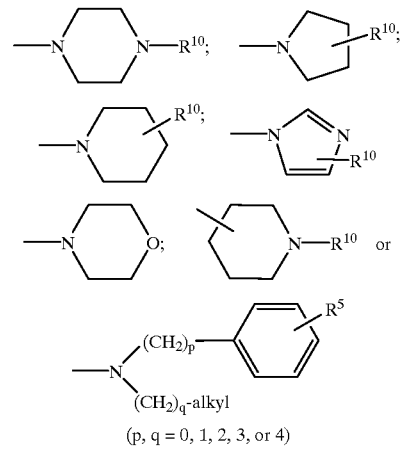

(p, q = 0, 1, 2, 3, or 4)

$R^9$ is hydrogen, $C_1$–$C_4$-alkyl, —O—$C_1$–$C_4$-alkyl, OH, Cl, F, Br, I, $CF_3$, $NO_2$, $NH_2$, CN, COOH, COO—$C_1$–$C_4$-alkyl, —NHCO—$C_1$–$C_4$-alkyl, —NHCO-phenyl, —NHSO$_2$—$C_1$–$C_4$-alkyl, —NHSO$_2$-phenyl, —SO$_2$—$C_1$–$C_4$-alkyl or —SO$_2$-phenyl, $R^{10}$ is hydrogen or $C_1$–$C_6$-alkyl which can be substituted by a phenyl ring which can also be substituted by one or two $R^9$ radicals, n is the number 0, 1 or 2, m is the number 0, 1, 2, 3 or 4, and o is the number 0, 1, 2, 3 or 4.

2. A ketobenzamide of the formula I as claimed in claim 1, where $R^2$ is hydrogen, $C_1$–$C_4$-alkyl, fluorine or chlorine, $R^3$ is —$CH_2$—phenyl, —$CH_2$-cyclohexyl, n-butanyl or n-pentanyl, each of which can be substituted by an $R^5$ radical, $R^4$ is —$NR^8$, and $R^1$, X and n have the meanings given in claim 1.

3. A method of controlling disorders mediated by calpain enzymes comprising administering to a host in need thereof an effective amount of a ketobenzamide of the formula I as claimed in claim 1.

4. A drug preparation which comprises at least one ketobenzamide of the formula I as claimed in claim 1.

* * * * *